(12) United States Patent
Toth et al.

(10) Patent No.: US 7,312,194 B2
(45) Date of Patent: Dec. 25, 2007

(54) DELIVERY SYSTEMS

(75) Inventors: Istvan Toth, Moggill (AU); Robert Falconer, Gillingham (GB); Shaun Emmanuel De Cruz, Taringa (AU); Ross Peter McGeary, St. Lucia (AU); Benjamin Paul Ross, Chapel Hill (AU)

(73) Assignee: Alchemia Pty. Ltd., Queensland (AU)

( * ) Notice: Subject to any disclaimer, the term of this patent is extended or adjusted under 35 U.S.C. 154(b) by 0 days.

(21) Appl. No.: 10/676,436

(22) Filed: Jun. 30, 2003

(65) Prior Publication Data

US 2004/0176281 A1    Sep. 9, 2004

Related U.S. Application Data

(63) Continuation-in-part of application No. PCT/AU02/00005, filed on Jan. 3, 2002.

(30) Foreign Application Priority Data

Jan. 4, 2001  (GB) ................. 0100115.5

(51) Int. Cl.
A61H 38/14 (2006.01)
A61K 38/16 (2006.01)
A61K 31/715 (2006.01)
(52) U.S. Cl. .................. 514/8; 514/54; 536/1.11; 536/18.7
(58) Field of Classification Search ............ 514/8, 514/54; 536/18.7, 1.11
See application file for complete search history.

(56) References Cited

OTHER PUBLICATIONS

Goodman & Gillman's, The Pharmacological Basis of Therapeutics, 10th Ed., 2001, pp. 54-57.*
Dekany et al , Peptides, 1996, 331-32.*
Dekany et al Peptides, 1996, 331-32.*
Neubert Pharmaceutical Research, 1989, 6(9), 743-749.*
Chemical Abstract No. 133:242515, Toth et al., *Proc. Eur. Pept. Symp.*, 25th, pp. 48-49, 1999.
Chemical Abstract No. 129:331004, Dekany et al., *Proc. Eur. Pept. Symp.* 24th, pp. 331-332, 1998.
Dubber et al., "Synthesis of Octopus Glycosides: Core Molecules for the Construction of Glycoclusters and Carbohydrate-Centered Dendrimers," *Carbohydrate Research*, 310:35-41, 1998.
Gould and Holman, "The Glucose Transporter Family: Structure, Function and Tissue-Specific Expression," *Biochem. J.*, 295:329-341, 1993.
Green and Hadgraft, "Facilitated Transfer of Cationic Drugs Across a Lipoidal Membrane by Oleic Acid and Lauric Acid," *Int. J. Pharm.*, 37:251-252, 1987.
Hadgraft et al., "Facilitated Transport of Sodium Salicylate Across an Artificial Lipid Membrane by Azone," *J. Pharm. Pharmacol.*, 37:725-727, 1985.
Lee et al., "Mucosal Penetration Enhancers for Facilitation of Peptide and Protein Drug Absorption," *Crit. Rev. Thera. Drug Carrier Sys.*, 8(2):91-192, 1991.
Meyer and Manning, "Hydrophobic Ion Pairing: Altering the Solubility Properties of Biomolecules," *Pharm. Res.*, 15(2):188-193, 1998.
Mizuma et al., "Factors that Cause the β-Anomeric Preference of $Na^+$/Glucose Cotransporter for Intestinal Transport of Monosaccharide Conjugates," *Biochim. Biophysica. Acta*, 1381:340-346, 1998.
Neubert, "Ion Pair Transport Across Membranes," *Pharm. Res.*, 6(9):743-747, 1989.
Nomoto et al., "Improvement of Intestinal Absorption of Peptide Drugs by Glycosylation: Transport of Tetrapeptide by the Sodium Ion-Dependent D-Glucose Transporter," *J. Pharm. Sci.*, 87(3):326-332, 1998.
Quintanar-Guerrero et al., "Applications of the Ion-Pair Concept to Hydrophilic Substances with Special Emphasis on Peptides." *Pharm. Res.*, 14(2):119-127, 1997.
International Search Report for PCT/AU02/00005, mailed Mar. 28, 2002.

* cited by examiner

*Primary Examiner*—Shaojia Anna Jiang
*Assistant Examiner*—Ganapathy Krishnan
(74) *Attorney, Agent, or Firm*—Haynes and Boone LLP; Mark D. Moore

(57) ABSTRACT

The invention relates to compounds which are useful in the delivery of a wide variety of therapeutically useful molecules. In particular, the invention relates to compounds which are able to act as carriers for therapeutically useful molecules, and to pharmaceutical agents comprising these carriers. The compounds of the invention comprise a mono- or oligosaccharide, a lipidic moiety, and optionally a linker and/or a spacer. The pharmaceutical agents of the invention are particularly useful for oral administration.

32 Claims, 2 Drawing Sheets

DELIVERY SYSTEMS

CROSS-REFERENCE TO RELATED APPLICATIONS

This application is a continuation-in-part of International Application No. PCT/AU02/00005, filed Jan. 3, 2002, designating the United States; which claims the priority of British Application No. 0100115.5, filed Jan. 4, 2001. The entire contents of these two applications are incorporated into this application by reference.

FIELD OF THE INVENTION

The invention relates to compounds which are useful in the delivery of a wide variety of therapeutically useful molecules. In particular, the invention relates to compounds which are able to act as carriers for therapeutically useful molecules, and to pharmaceutical agents comprising these carriers. The compounds of the invention comprise a mono- or oligosaccharide, a lipidic moiety, and optionally a linker and/or a spacer. The pharmaceutical agents of the invention are particularly useful for oral administration.

BACKGROUND OF THE INVENTION

It will be clearly understood that, although a number of prior art publications are referred to herein, this reference does not constitute an admission that any of these documents forms part of the common general knowledge in the art, in Australia or in any other country.

The successful development of any medicinal compound relies on specific and potent pharmacological activity combined with efficient delivery of the molecule to its target site. Many potential drugs and medicinal peptides fail to reach the marketplace due to poor bioavailabillity.

Poor oral absorption presents a significant barrier to the clinical success of many drugs, particularly peptides. Drug delivery strategies seek to overcome the physical and chemical properties responsible for this poor bioavailabillity, including molecular size, charge, hydrophilicity, hydrogen bonding potential and enzymatic lability. There are only a few reliable examples of therapeutic levels for peptides and proteins being achieved via the oral route.

A number of approaches have been employed to improve oral bioavailabillity for therapeutic molecules. These include the use of penetration enhancers, which alter membrane permeability non-specifically [Lee, V. H. L.; Yamamoto, A.; Kompella, U. B. *Crit. Rev. Ther. Drug Carrier Syst.*, 1991, 8, 91-192.], the use of drug delivery systems such as liposomes, microparticles and microemulsion systems which protect the drug from the environment, and the use of prodrugs which modify the drug molecule itself to impart the desired physicochemical properties.

It is believed that the more lipophilic the molecule, the faster and more completely a drug molecule crosses the intestinal barrier. There is a danger, however, of making a drug too lipophilic for epithelial transport. Results suggest that there is a degree of lipophilicity which is "optimal" for absorption. Highly lipophilic drugs suffer from poor aqueous solubility, which is also necessary for successful oral uptake.

Occasionally hydrophilic drug molecules show unexpectedly high rates of oral absorption. Two mechanisms have been proposed to explain this effect. Active transport systems can be accessed by some molecules resulting in the "pumping" of hydrophilic molecules into the body. Alternatively, ion pair transport has been proposed to explain the unexpected absorption of highly hydrophilic drugs such as the tetracyclines, which are charged over the range of physiological conditions, and are generally lipid-insoluble [Meyer, J. D.; Manning, M. C.; Hydrophobic Ion Pairing: Altering the Solubility Properties of Biomolecules. *Pharm. Res.*, 1998, 15, 188-193]. The interaction of such drugs with endogenous counter-ions in effect "buries" the charge within the ion pair, forming a neutral species, which may be able to traverse the epithelium. Hydrophobic ion pairing represents an inexpensive and reversible means by which to modify the physicochemical properties of a drug without the need for irreversible chemical modification [Neubert, R. Ion Pair Transport Across Membranes. *Pharm. Res.*, 1989, 6, 743-747].

The ability to form an ion pair and the success of improving transport by this approach depends very greatly on the physicochemical properties of both the drug and the counter-ion.

An ion pair can be defined as a neutral species formed by electrostatic attraction between oppositely charged ions in solution, which are often sufficiently lipophilic to dissolve in non-aqueous solvents [Quintanar-Guerrero, D.; Allemann, E.; Fessi, H.; Doelker, E. Applications of the Ion-Pair Concept to Hydrophilic Substances with Special Emphasis on Peptides. *Pharm. Res.*, 1997, 14, 119-127.].

The lipophilicity of hydrophilic ionised drugs can be increased by ion pair formation with lipophilic counter-ions such as hexylsalicylate or decylsulphate. It appears that ion pair formation only affects the partition and transport of hydrophilic drugs which are charged in the media in which ion pairing takes place.

Although counter-ions such as alkylsulphates, trichloroacetate and alkylcarbonates have been used for ion pairing, it has been suggested that these counter-ions are too irritant to the gut at the required dosages [Neubert, et al op. cit.]. *Pharm. Res.*, 1989, 6, 743-747 and references here-in]. Counter-ions need to have the following properties: high lipophilicity, sufficient solubility, physiological compatibility and metabolic stability. Suitable counter-ions include alkanoic acids [Green, P. G.; Hadgraft, J. *Int. J. Pharm.*, 1987, 37, 251-255] and alkylated salicylic acids [Neubert, R. Ion Pair Transport Across Membranes. *Pharm. Res.*, 1989, 6, 743-747].

It was initially supposed that the two components of an ion pair traverse lipid membranes at an equimolar ratio. However, the mechanism may be more complex. Experiments based on lipophilic counter-ions for cationic drug transport showed that the counter-ions accumulated in the membrane, and that, as a result, more hydrophilic drug molecules than counter-ions were transported. Transport of the complete ion pair was also demonstrated. (Neubert et al. 1989 op. cit.]. A similar mechanism has been proposed for the transport of anionic drugs [Hadgraft, J.; Wotton, P. K.; Walters, K. A. *J. Pharm. Pharmacol.*, 1985, 37, 757-727].

The approaches discussed thus far are based on increasing lipophilicity for enhanced transport by passive diffusion via the transcellular pathway. An alternative strategy is to exploit the numerous active transport mechanisms present in the gastrointestinal mucosa. Strategies have been designed to improve the bioavailability of poorly absorbed drugs and peptides so that they can be absorbed by specialised intestinal transporters.

Conjugation of a saccharide moiety to a poorly absorbed drug improves its solubility in aqueous media due to the poly-hydroxyl nature of sugars. In addition, sugar conjugation may allow passage of the sugar-drug conjugate across the gut via the SGLT-1 glucose transporter [Gould, G. W.; Holman G. D. The Glucose transporter family: structure, function and tissue-specific expression. *Biochem. J.,* 1993, 295, 329-341]. The effectiveness of this approach has been demonstrated by conjugation of a glucose derivative to a tetrapeptide not normally transported by PepT1 [Nomoto, M.; Yamada, K.; Haga, M.; Hayashi, M. Improvement of Intestinal Absorption of Peptide Drugs by Glycosylation: Transport by the Sodium Ion-Dependent D-Glucose Transporter. *J. Phar. Sci.,* 1998, 87, 326-332]. Interestingly, the configuration at the anomeric centre of the sugar was found to affect the rate of transport: A β-anomeric linkage was preferred over the α-configuration. Subsequently, further evidence was presented for glycosides of paracetamol [Mizuma, T.; Nagamine, Y.; Dobashi, A.; Awazu, S. Factors that cause the β-anomeric preference of Na+/glucose cotransporter for intestinal transport of monosaccharides conjugates. *Biochim. Biophys. Acta,* 1998, 1381, 340-346]. Glucose conjugates were transported more efficiently than galactose conjugates, with the β-trans-anomeric configuration preferred in both cases. Galactose conjugates with the α-cis-configuration were not transported at all.

We have previously demonstrated the utility of conjugating lipoamino acids or lipoaminosaccharide constructs to drug molecules through a covalent bond (International Patent Application No. PCT/AU01/01313 filed 18 Oct. 2001; Toth et al., 1993; Toth and Gibbons, British Patent Application No. 9215780.9 (24 Jul. 1992); Toth and Gibbons, European Patent Application No. 93917902.4). These compounds provide an excellent delivery system, but require the chemical conjugation of the drug molecule to the delivery system.

We now propose the use of lipoamino acids and lipoaminosaccharide conjugates as an ionic delivery system in which the drug molecule and the delivery system form an ionic complex. This system does not require the chemical conjugation of the drug molecule, and therefore will not alter the pharmacological properties of the drug molecule. In addition, this method of delivery can be used to target either passive or active transport mechanisms. The proposed delivery system is readily optimised for hydrophilic drug molecules, peptides and proteins, and offers significant benefits in terms of regulatory approval. We believe that this is the first example of the use of non-covalently linked lipoamino acids and lipoamino saccharides for drug delivery.

SUMMARY OF THE INVENTION

In a general aspect, the invention provides a compound of general formula I:

r[D$^{(nz)}$]p[(W$_q$—S—X-L)$^{(my)}$]     formula I in which D is a therapeutically useful molecule, such as a drug, peptide, protein, nucleic acid, mono- or oligosaccharide, sugar-amino acid conjugate, sugar-peptide conjugate, nucleic acid, pro-drug or drug-like molecule;

r is an integer equal to or greater than 1;

p, n and m may be the same or different, and are independently integers equal to or greater than 1;

n and m represent the overall magnitude of the charge on the molecules; and z and y are charges, either positive (+) or negative (−), such that when z is positive, y must be negative and vice versa;

and [(Wq—S—X-L)$^{(my)}$] is a carrier compound, in which

X is a covalent bond, or is a linker group, selected from 2 to 14 atom spacers, which may be substituted or unsubstituted, branched or linear;

S is a mono- or oligosaccharide, which may be of natural or synthetic origin;

L is a lipidic moiety, as defined herein;

W may be absent, or is a 3 to 10 atom alkyl or heteroalkyl spacer, which may be branched or linear, and is substituted with one or more functional groups, each of which is charged or is capable of carrying a charge under physiological conditions; and q is 0 when W is absent, or is an integer which ranges from 3 to the number of hydroxyls available for substitution on the mono- or oligosaccharide; for example, when S is a monosaccharide, q may be 0, 3 or 4; when S is a disaccharide, q may be 0 or 3 to 7.

In one preferred embodiment of the invention, r is an integer equal to or greater than 1, and the compound is an ionic complex between a carrier compound of general formula V

[(W)$_q$—S—X-L)$^{(my)}$]     formula V and a therapeutically useful molecule D. Compounds according to this embodiment are useful as pharmaceutical agents for delivery of active compounds, especially for oral administration.

In the case of biological molecules, for example DNA, n and m may be relatively high or indeterminate. For example, if the biological molecule is a nucleic acid, n and m may be many hundreds; if it is a polysaccharide, n and m may be very large, up to many hundreds, and may vary from molecule to molecule. The person skilled in the art will readily be able to judge in any given case whether n and m need to be determined, and how to do so if this is necessary.

It will be apparent that the values n and m are not required to be equal, and that there is no requirement for the complex to be neutral. It will be further apparent that there is no requirement for the drug and carrier to be in stoichiometric amounts, and that the drug may be present in large excess over the carrier or vice versa, if this is required to effect efficient delivery of the drug molecule.

The linker X may be attached to the mono- or oligosaccharide S through the glycosidic position, or via any other suitable position on the mono- or oligosaccharide, by methods known in the art. Examples of such linkages include, but are not limited to O-glycoside, C-glycoside, N-glycoside, S-glycoside, amide, urea, thiourea, carbamate, thiocarbamate, carbonate, ether and ester bonds. Similarly the linker X may be attached to the lipidic moiety L by methods known to those skilled in the art, including but not limited to amide, ester, ether, imine, carbamate, urea, thiourea, or carbonate linkages.

Examples of suitable functional groups W include, but are not limited to, amidine, guanidinium, carboxylate, tetrazole, hydroxamic acid, hydrazide, amine, sulfate, phosphonate, phosphate, and sulfonate. It will be apparent that these functional groups may be the same or different, and may be of differing charge, so as to confer suitable properties on the carrier molecule.

The lipidic moiety L is composed of:

(a) any combination of 1 to 4 lipoamino acids and/or lipoamino alcohols, of general formula IIa or IIb

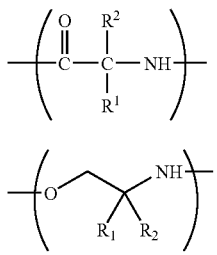

in which each of $R^1$ and $R^2$ may independently be:

(i) hydrogen, or (ii) a linear or branched chain alkyl or alkenyl group having 4 to 24 carbon atoms, which may optionally be substituted, provided that the substituents do not significantly adversely affect the lipophilic nature of the group, with the proviso that both $R^1$ and $R^2$ cannot be hydrogen at the same time;

(b) a glycerol-based lipid of general formula IIIa or IIIb

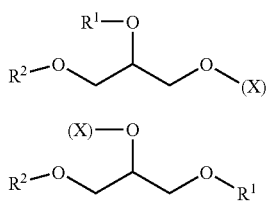

in which $R^1$ and $R^2$ are as defined in general formula IIa, and

X is a linker group, as defined in general formula I; or (c) a trishydroxymethylmethylamine-based lipid of general formula IVa or IVb

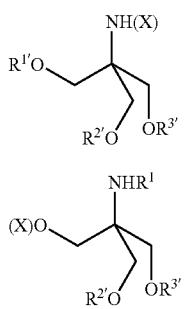

in which $R^{1'}$, $R^{2'}$ and $R^{3'}$ are independently hydrogen; a linear or branched chain alkyl or alkenyl group having 4 to 24 carbon atoms; or an aryl or arylalkyl group having 6 to 24 carbon atoms, in which the alkyl, alkenyl, aryl or arylalkyl groups may optionally be substituted, provided that the substituents do not significantly adversely affect the lipophilic nature of the group, and with the proviso that at least one of $R^{1'}$, $R^{2'}$ and $R^{3'}$ is not hydrogen; and X is as defined in general formula I.

The lipidic moiety L may optionally contain one or more charged functional groups, such as amidine, guanidinium, carboxylate, tetrazole, hydroxamic acid, hydrazide, amine, sulfate, phosphonate, phosphate, or sulfonate. It will be apparent that these functional groups may be the same or different, and may be of differing charge, so as to confer suitable properties on the carrier compound.

In a first preferred embodiment of the invention, r is equal to or greater than 1, and the compounds are useful as pharmaceutical agents.

In a particularly preferred embodiment, the invention provides a compound of general formula I in which the mono- or oligosaccharide S is a mono-, di- or tri-saccharide, and the lipidic moiety is one to three lipoaminoacids of general formula IIa or IIb.

In another particularly preferred embodiment the compound is piperacillin/2-acetamido-2-deoxy-N-(1-amino-(R/S)-dodecoyl)-β-D-glucopyranosylamine ionic complex.

In a second preferred embodiment, r is 0, and the compound is of general formula V:

in which W, S, X, L, m, q and y are as defined in General Formula I. Compounds in which r is 0 are useful as carrier compounds in the pharmaceutical agents of the invention.

In a second aspect, the invention provides a method of preparing a compound of general formula V, comprising the step of forming a covalent bond between the mono- or oligosaccharide S and the linker X or the lipid L, in which the bond between S and X is an O-glycoside, C-glycoside, N-glycoside, S-glycosides, amide, urea, thiourea, carbamate, thiocarbamate, carbonate, ether or ester bond, and the bond between X and L is an amide, ester, ether, imine, carbamate, urea, thiourea, or carbonate bond.

In a third aspect, the invention provides a composition comprising a compound according to the first aspect of the invention, together with a pharmaceutically-acceptable carrier.

In a fourth aspect, the invention provides a method of preparation of a pharmaceutical agent of general formula I, comprising the step of mixing a drug molecule D with a carrier compound of general formula V in solution, thereby to form an ionic complex, followed by removal of the solvent(s) to provide a homogeneous mixed salt.

In a fifth aspect, the invention provides a method of delivery of a therapeutically useful molecule, comprising the step of administering the molecule to a subject in need of such treatment in the form of a pharmaceutical agent of general formula I. Preferably the administration is oral.

In a sixth aspect, the invention provides a method of treating or preventing a pathological condition, comprising the step of administering a suitable pharmaceutical agent according to the invention to a subject in need of such treatment.

The subject may be a human, or may be a domestic or companion animal. While it is particularly contemplated that the compounds of the invention are suitable for use in medical treatment of humans, they are also applicable to veterinary treatment, including treatment of companion animals such as dogs and cats, and domestic animals such as horses, cattle and sheep, or zoo animals such as felids, canids, bovids, and ungulates.

Methods and pharmaceutical carriers for preparation of pharmaceutical compositions are well known in the art, as set out in textbooks such as Remington's Pharmaceutical Sciences, 19th Edition, Mack Publishing Company, Easton, Pa., USA.

The carrier or diluent, and other excipients, will depend on the route of administration, and again the person skilled in the art will readily be able to determine the most suitable formulation for each particular case.

For the purposes of this specification it will be clearly understood that the word "comprising" means "including but not limited to", and that the word "comprises" has a corresponding meaning.

DETAILED DESCRIPTION OF THE INVENTION

S may be a natural or synthetic monosaccharide, or an oligosaccharide preferably having 1 to 6 monosaccharide moieties. Non-limiting examples include glucose, glucosamine, galactose, mannose, glucuronic acid, iduronic acid, idose, fucose, galactosamine, sucrose, fructose, maltose, lactose, lactosamine, globotriose, globotetraose, chitobiose, chitotriose, chitotetraose, chitopentaose, chitohexaose, galabiose$\alpha$1, 3-galactobiose, Gal $\alpha$1,3-Gal $\beta$1,4-GlcNAc, mannobiose, cellobiose, cellopentaose, cellotetraose, cellotriose, ribose, arabinose, trigalacturonic acid, or maltotriose which may be branched or linear.

It will be understood that the value of q will depend on the number of available carbohydrate functional groups on the mono- or oligosaccharide S.

Typically, the available functional groups on S will be free hydroxyl, amino and/or carboxylate groups. For example, where S is a monosaccharide, q is an integer from 2 to 5; when S is a disaccharide, q is an integer from 2 to 7; where S is a trisaccharide, q is an integer from 2 to 10, and so on.

The therapeutically useful moiety D may be selected from synthetic or natural peptides, proteins, mono- or oligosaccharides, sugar-amino acid conjugates, sugar-peptide conjugates, nucleic acids, drugs, pro-drugs or drug-like molecules. Specific examples include sulfated oligosaccharides, charged oligosaccharides, sulfated antithrombotics or aminoglycosides.

The linker X may be a covalent bond, or may be a) a monosaccharide or disaccharide moiety, which modifies the physicochemical properties of the compound, such as water solubility, targets the compound to specific sites such as mannose, targets an active uptake mechanism such as the glucose transport system, and/or modifies the immune response;

b) a spacer alkyl, alkenyl, alkynyl, heteroalkyl, arylalkyl, or heteroarylalkyl group of 2 to 14 atoms in length, which may optionally be substituted, or may be branched or linear, which separates the lipidic moiety L from the mono- or oligosaccharide S;

c) a peptide or amino acid which modifies the physicochemical properties of the compound, or which provides suitable spacing between the lipidic moiety L and the mono- or oligosaccharide S; or d) a combination of two or more of the above-mentioned groups a) to c).

Suitable spacer groups (b) include polyethyleneglycol or polyglycine. It may be convenient to include substituents so as to confer suitable solvent solubility properties upon the system. Examples of suitable substituents include functional groups which modify the polarity or solvation of the linker, such as $CO_2H$, $NH_2$, SH, OH, or halo. X may be attached to the mono- or oligosaccharide S by one or more linkage methods known in the art, such as ether, ester, carbamate, urea or amide linkages.

The lipoamino acids in the lipidic moiety L may be coupled sequentially, or may be interspersed with up to 4 other amino acid spacers such as serine or arginine which modify properties such as the solubility of L.

The term "alkyl" denotes straight chain, branched or cyclic alkyl, preferably $C_{1-30}$alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methylhexyl, 1-methylhexyl, 2,2-dimethypentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2 pentylheptyl and the like.

Examples of cyclic alkyl groups include mono- or polycyclic alkyl groups such as cyclopropyl, cyclobutyl, cyclopentyl, cyclohexyl, cycloheptyl, cyclooctyl, cyclononyl, cyclodecyl and the like.

The term "alkenyl" denotes groups formed from straight chain, branched or cyclic alkenes including ethylenically mono-, di- or poly-unsaturated alkyl or cycloalkyl groups as defined above, preferably $C_{2-20}$alkenyl. Examples of alkenyl include vinyl, allyl, 1-methylvinyl, butenyl, iso-butenyl, 3-methyl-2-butenyl, 1-pentenyl, cyclopentenyl, 1-methylcyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl; 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl.

The term "alkynyl" denotes groups formed from straight chain, branched, or mono- or poly- or cyclic alkynes. Examples of alkynyl include ethynyl, 1-propynyl, 1- and 2-butynyl, 2-methyl-2-propynyl, 2-pentynyl, 3-pentynyl, 4-pentynyl, 2-hexynyl, 3-hexylnyl, 4-hexynyl, 5-hexynyl, 10-undecynyl, 4-ethyl-1-octyn-3-yl, 7-dodecynyl, 9-dodecynyl, 10-dodecynyl, 3-methyl-1-dodecyn-3-yl, 2-tridecynyl, 11-tridecynyl, 3-tetradecynyl, 7-hexadecynyl, 3-octadecynyl and the like.

The term "aryl" used either alone or in compound words such as "heteroaryl" denotes single, polynuclear, conjugated and fused residues of aromatic hydrocarbons or aromatic heterocyclic ring systems. Examples of aryl include phenyl, biphenyl, terphenyl, quaterphenyl, phenoxyphenyl, naphthyl, tetrahydronaphthyl, anthracenyl, dihydroanthracenyl, benzanthracenyl, dibenzanthracenyl, phenanthrenyl, fluorenyl, pyrenyl, indenyl, azulenyl, chrysenyl, pyridyl, 4-phenylpyridyl, 3-phenylpyridyl, thienyl, furyl, pyrryl, pyrrolyl, furanyl, imadazolyl, pyrrolydinyl, pyridinyl, piperidinyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferably, the aromatic heterocyclic ring system contains 1 to 4 heteroatoms independently selected from N, O and S and containing up to 9 carbon atoms in the ring.

The expression "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, aryloxy, carboxy, benzyloxy, haloalkoxy, haloalkenyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acylamino, acyl, alkenylacyl, alkynylacyl, arylacyl, acylamino, acyloxy, aldehydo, alkylsulphonyl, arylsulphonyl, sulphonylamino, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, sulfonic acid, alkylthio, arylthio and acylthio.

The term "halo" denotes fluorine, chlorine, bromine or iodine.

The term "subject" as used herein refers to any animal having a disease or condition which requires treatment with a pharmaceutically-active agent. The subject may be a human, or may be a domestic or companion animal. While it is particularly contemplated that the compounds of the invention are suitable for use in medical treatment of humans, it is also applicable to veterinary treatment, including treatment of companion animals such as dogs and cats, and domestic animals such as horses, cattle and sheep, or zoo animals such as felids, canids, bovids, and ungulates.

As used herein, the term "therapeutically effective amount" means an amount of a compound of the present invention effective to yield a desired therapeutic response, for example to prevent or treat a disease which by administration of a pharmaceutically-active agent.

The specific "therapeutically effective amount" will, obviously, vary with such factors as the particular condition being treated, the physical condition and clinical history of the subject, the type of animal being treated, the duration of the treatment, the nature of concurrent therapy (if any), and the specific formulations employed and the structure of the compound or its derivatives.

As used herein, a "pharmaceutical carrier" is a pharmaceutically acceptable solvent, suspending agent, excipient or vehicle for delivering the compound of formula I and/or pharmaceutically-active agent to the subject. The carrier may be liquid or solid, and is selected with the planned manner of administration in mind.

The pharmaceutical agent may be administered orally, topically, or parenterally in dosage unit formulations comprising conventional non-toxic pharmaceutically-acceptable carriers, adjuvants, and vehicles. The term parenteral as used herein includes subcutaneous, intravenous, intramuscular, intrathecal, intracranial, injection or infusion techniques.

The invention also provides suitable topical, oral, aerosol, and parenteral pharmaceutical formulations for use in the novel methods of treatment of the present invention. The compounds of the invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the active ingredient in admixture with non-toxic pharmaceutically acceptable excipients which are suitable for the manufacture of tablets.

These excipients may be inert diluents, such as calcium carbonate, lactose, calcium phosphate or sodium phosphate; granulating and disintegrating agents, such as corn starch or alginic acid; binding agents, such as starch, gelatin or acacia; or lubricating agents, such as magnesium stearate, stearic acid or talc. The tablets may be uncoated, or may be coated by known techniques to delay disintegration and absorption in the gastrointestinal tract and thereby provide a sustained action over a longer period. For example, a time-delay material such as glyceryl monostearate or glyceryl distearate may be employed. Coating may also be performed using techniques described in U.S. Pat. Nos. 4,256,108; 4,160,452; and 4,265,874 to form osmotic therapeutic tablets for control release.

For in vivo application, the pharmaceutical agent of the invention can be administered, parenterally by injection or by gradual perfusion over time independently or together. Administration may be intravenously, intra-arterial, intraperitoneally, intramuscularly, subcutaneously, intracavity, or transdermally. For in vitro studies the agents may be added or dissolved in an appropriate biologically acceptable buffer and added to a cell or tissue.

Preparations for parenteral administration may include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers such as those based on Ringer's dextrose, and the like. Preservatives and other additives may also be present such as, for example, antimicrobials, anti-oxidants, chelating agents, growth factors and inert gases and the like.

It is envisioned that the invention can be used to prevent or treat any disease or condition susceptible to treatment with or alleviation by pharmaceutically-active agents, including neoplasms, cancers (eg cancers of the breast, lung, prostate, kidney, skin, neural, ovary, uterus, liver, pancreas, epithelial, gastric, intestinal, exocrine, endocrine, lymphatic, haematopoietic system or head and neck tissue), fibrotic disorders and the like; disorders of the central nervous system including Alzheimer's disease (AD) and other forms of dementia and memory loss, motor neurone diseases, disorders of cardiovascular system including cardiac hypertrophy, congestive heart failure, hypertension, hormonal imbalance, atherosclerosis, disorders of development and growth including, disorders of glucose and fat metabolism and the like.

Generally, the terms "treating", "treatment" and the like are used herein to mean affecting a subject, tissue or cell to obtain a desired pharmacological and/or physiological effect. The effect may be prophylactic in terms of completely or partially preventing a disease or sign or symptom thereof, and/or may be therapeutic in terms of a partial or complete cure of a disease. "Treating" as used herein covers any treatment of, or prevention of disease in a vertebrate, a mammal, particularly a human, and includes: preventing the disease from occurring in a subject that may be predisposed to the disease, but has not yet been diagnosed as having it; inhibiting the disease, ie., arresting its development; or relieving or ameliorating the effects of the disease, ie., cause regression of the effects of the disease.

The invention includes various pharmaceutical compositions useful for ameliorating disease. The pharmaceutical compositions according to one embodiment of the invention are prepared by bringing a compound of formula I, analogue, derivatives or salts thereof and one or more pharmaceutically-active agents or combinations of compound of formula I and one or more pharmaceutically-active agents into a form suitable for administration to a subject using carriers, excipients and additives or auxiliaries.

Frequently used carriers or auxiliaries include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol and polyhydric alcohols. Intravenous vehicles include fluid and nutrient replenishers. Preservatives include antimicrobial, anti-oxidants, chelating agents and inert gases. Other pharmaceutically acceptable carriers include aqueous solutions, non-toxic excipients, including salts, preservatives, buffers and the like, as described, for instance, in Remington's Pharmaceutical Sciences, 15th ed. Easton: Mack Publishing Co., 1405-1412,1461-1487 (1975) and The National Formulary XIV., 14th ed. Washington: American Pharmaceutical Association (1975), the contents of which are hereby incorporated by reference. The pH and exact concentration of the various components of the pharmaceutical composition are adjusted according to routine skills in the art. See Goodman and Gilman's The Pharmacological Basis for Therapeutics (7th ed.).

The pharmaceutical compositions are preferably prepared and administered in dosagee units. Solid dosage units include tablets, capsules and suppositories. For treatment of a subject, depending on activity of the compound, manner of administration, nature and severity of the disorder, age and body weight of the subject, different daily doses can be used. Under certain circumstances, however, higher or lower daily doses may be appropriate. The administration of the daily dose can be carried out both by single administration in the form of an individual dose unit or else several smaller dose units and also by multiple administration of subdivided doses at specific intervals.

The pharmaceutical compositions according to the invention may be administered locally or systemically in a therapeutically effective dose. Amounts effective for this use will, of course, depend on the severity of the disease and the weight and general state of the subject. Typically, dosages used in vitro may provide useful guidance in the amounts useful for in situ administration of the pharmaceutical composition, and animal models may be used to determine effective dosages for treatment of the cytotoxic side effects. Various considerations are described, eg., in Langer, Science, 249: 1527, (1990). Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such excipients may be suspending agents such as sodium carboxymethyl cellulose, methyl cellulose, hydroxypropyl-methylcellulose, sodium alginate, polyvinylpyrrolidone, gum tragacanth and gum acacia; dispersing or wetting agents, which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleaginous suspension. This suspension may be formulated according to known methods using suitable dispersing or wetting agents and suspending agents such as those mentioned above. The sterile injectable preparation may also a sterile injectable solution or suspension in a non-toxic parenterally-acceptable diluent or solvent, for example, as a solution in 1,3-butanediol. Among the acceptable vehicles and solvents which may be employed are water, Ringer's solution, and isotonic sodium chloride solution. In addition, sterile, fixed oils are conventionally employed as a solvent or suspending medium. For this purpose, any bland fixed oil may be employed, including synthetic mono-or diglycerides. In addition, fatty acids such as oleic acid find use in the preparation of injectables.

Compounds of formula I may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Dosage levels of the compound of formula I of the present invention will vary, depending on the activity of the drug molecule D, but will usually be of the order of about 0.5 µg to about 20 mg per kilogram body weight, with a preferred dosage range between about 0.5 µg to about 10 mg per kilogram body weight per day (from about 1 mg to about 3 g per patient per day). The amount of active ingredient which may be combined with the carrier materials to produce a single dosage will vary, depending upon the host to be treated and the particular mode of administration. For example, a formulation intended for oral administration to humans may contain about 1 mg to 1 g of an active compound with an appropriate and convenient amount of carrier material, which may vary from about 5 to 95 percent of the total composition. Dosage unit forms will generally contain between from about 1 mg to 500 mg of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. In particular, the person skilled in the art will be aware that some drugs are known to be effective at very low dosages.

In addition, some of the compounds of the invention may form solvates with water or common organic solvents. Such solvates are encompassed within the scope of the invention.

The compounds of the invention may additionally be combined with other compounds to provide an operative combination. It is intended to include any chemically compatible combination of pharmaceutically-active agents, as long as the combination does not eliminate the activity of the compound of formula I of this invention.

BRIEF DESCRIPTION OF THE DRAWINGS

In the Examples, reference will be made to the accompanying drawings in which.

EXAMPLES

Figure 1:
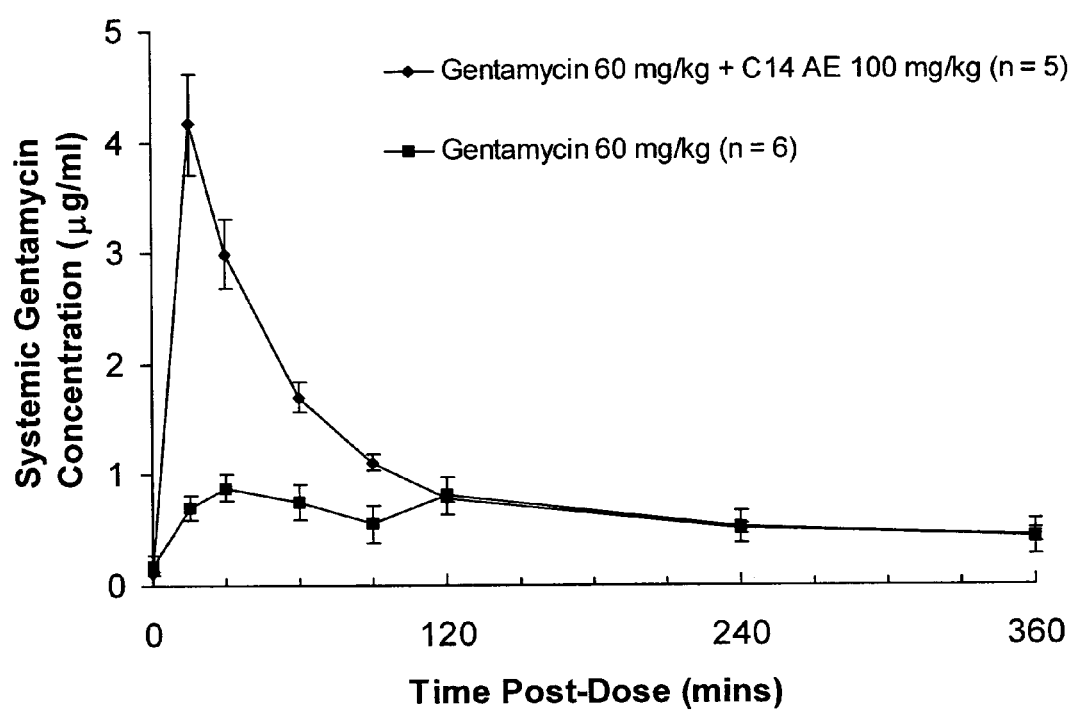
FIG. 1. is a graph showing mean (±SEM) plasma concentrations in male Sprague-Dawley rats following single bolus oral administration of gentamycin sulfate (GS) 60 mg/kg either with or without the liposaccharide absorption enhancer, C14 carboxylic acid (C14 AE) 100 mg/kg, as a function of time.

The invention will now be described with reference to the following non-limiting examples.

Examples 1 to 7 inclusive provide methods for the preparation of amide-linked mono, di and tri-saccharide-lipoamino acid complexes. The general reaction schemes are set out in Schemes 1 and 2, which relate to Example 1 to 4, Scheme 3, which follows on from Scheme 2 and relates to Examples 5 and 6, and Scheme 4, which follows on from Scheme 1, and relates to Examples 5 to 7.

Examples 8 to 16 inclusive provide methods for the preparation of complexes in which lipids are alternatively linked to the anomeric position of monosaccharides.

General schemes for synthesis of protected amide-linked charged monosaccharide- and polysaccharide lipoamino acid conjugates respectively are set out below.

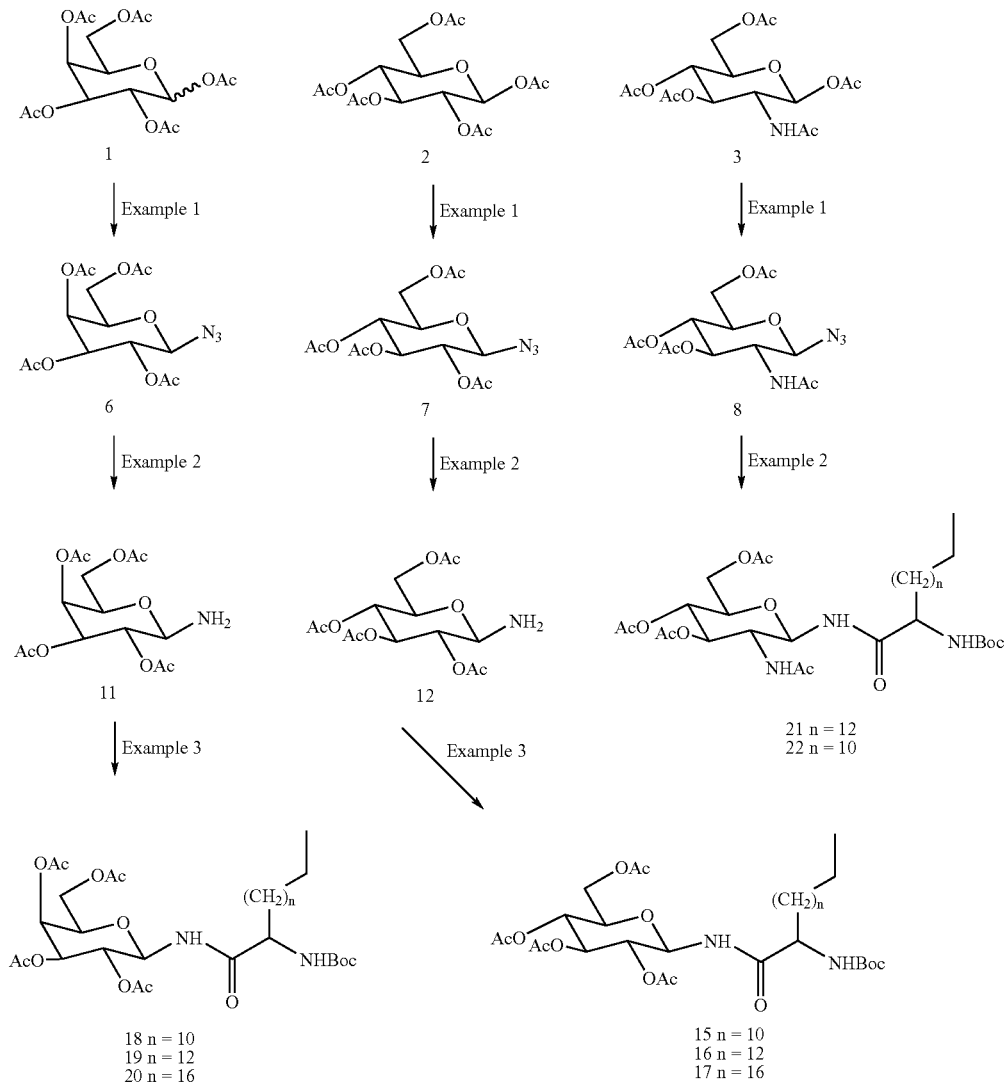

Scheme 1
Monosaccharide-lipoamino acid conjugates

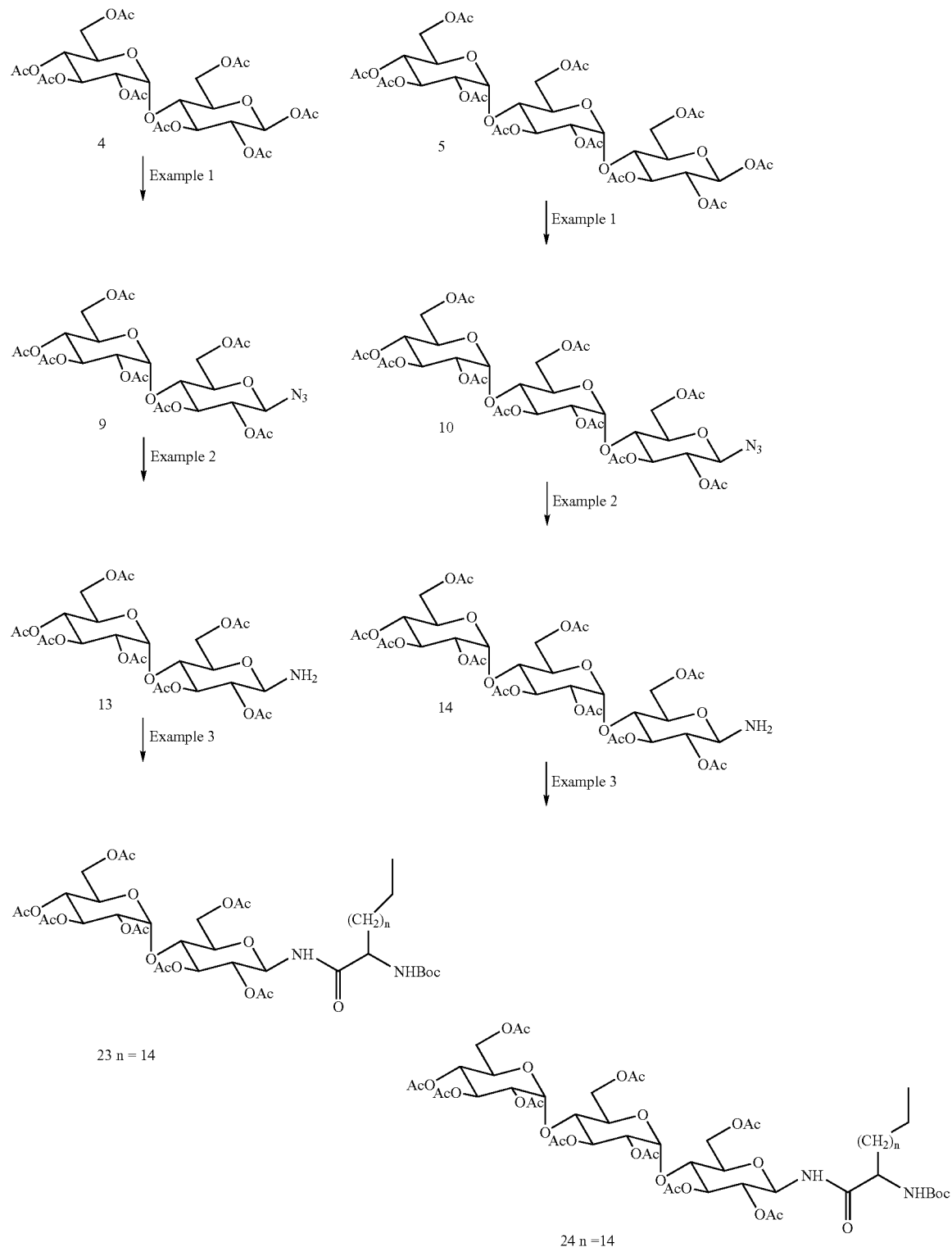

General scheme for deprotection of amide-linked charged oligosaccharide lipoamino acids.
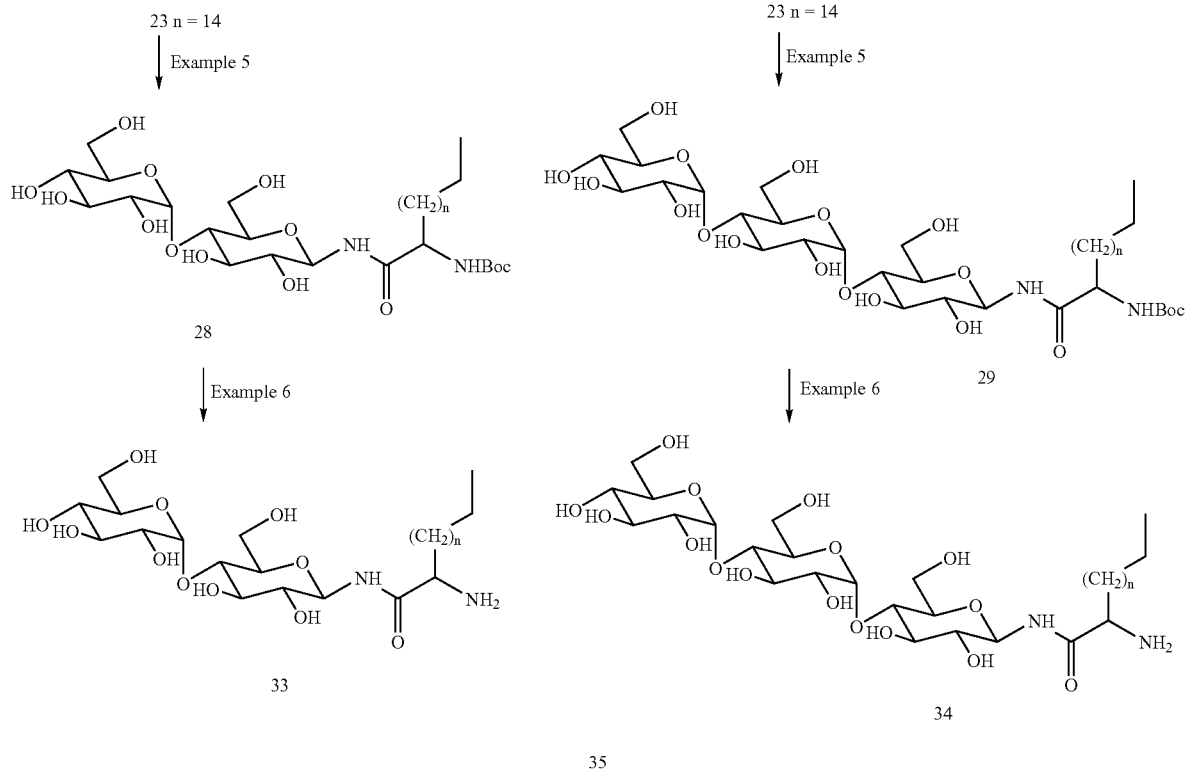
General scheme for deprotection of amide-linked charged monosaccharide lipoamino acid complexes and preparation of charged glycolipid—drug complexes.
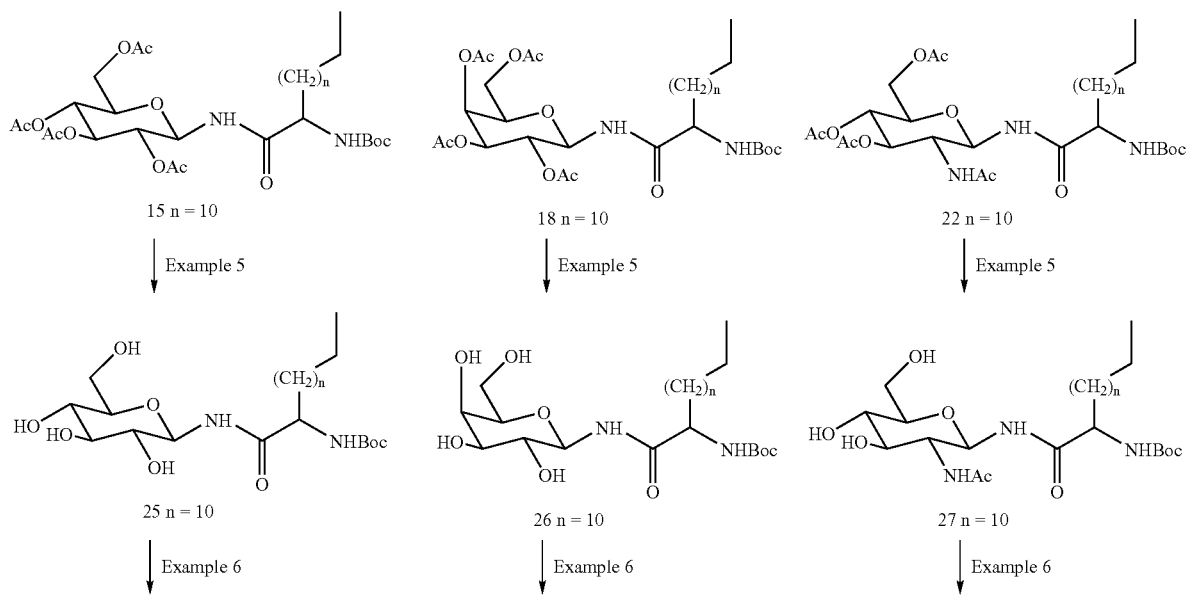

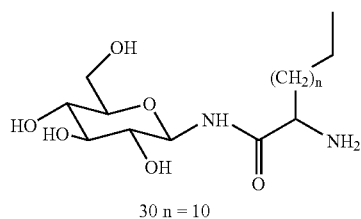

30 n = 10

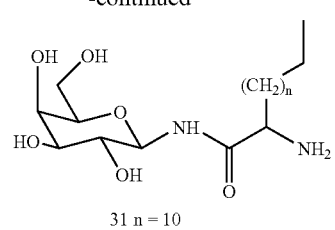

31 n = 10

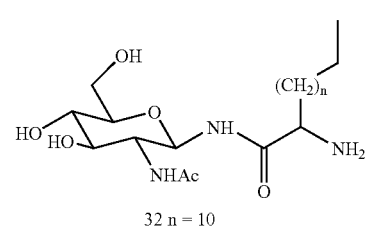

32 n = 10

↓ Example 7

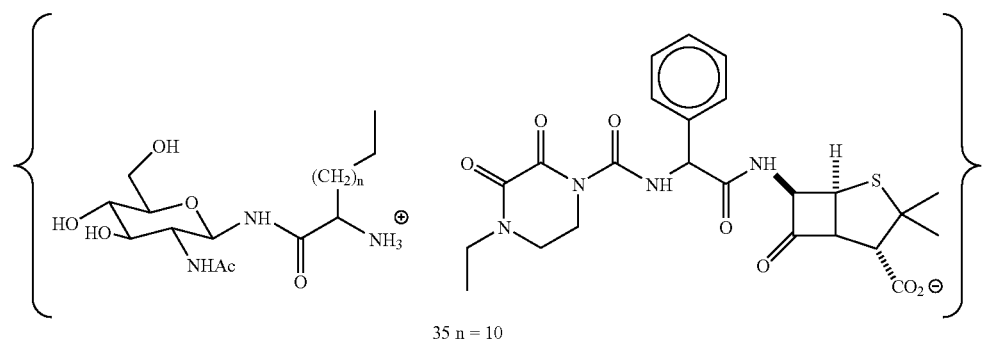

35 n = 10

30

Example 1

2,3,4,6-tetra-O-acetyl-β-D-galactopyranosyl azide (6)

1,2,3,4,6-penta-O-acetyl-α/β-D-galactopyranose (1)(10.0 g, 25.6 mmol) was dissolved in abs. $CH_2Cl_2$ (100 ml). Trimethylsilyl azide (7.38 g, 64.1 mmol) and tin(Iv) chloride (3.34 g, 12.8 mmol) were added to the solution, which was then stirred overnight. The reaction mixture was then diluted with $CH_2Cl_2$ (250 ml), washed with 1M $KF_{(aq)}$ (1×250 ml), brine (1×250 ml) and $NaHCO_{3(sat, aq)}$ (1×250 ml). The organic phase was dried over $MgSO_4$, filtered and evaporated. Recrystallisation from ethyl acetate:hexane 1:1 (v/v) gave (6) (8.62 g, 90%).

$R_F$=0.60 hexane:ethyl acetate 1:1 (v/v);

$^1H$ NMR δ 5.41 (d, 1H, H-4), 5.17 (m, 1H, H-2), 5.04 (m, 1H, H-3), 4.60 (d, 1H, H-1, $J_{1,2}$=8.7 Hz), 4.19 (m, 2H, H-6, H-6'), 4.00 (m, 1H, H-5), 2.15, 2.08, 2.05, 1.98 (4s, 12H, 4Ac);

FAB MS $C_{14}H_{19}N_3O_9$ (373.32) m/z (%) 396 [M+Na]$^+$ (100).

Cognate preparation of 2,3,4,6-tetra-O-acetyl-β-D-glucopyranosyl azide (7)

re-crystallisation from ethyl acetate:hexane 2:1 (v/v) gave (7) (7.87 g, 82%).

$R_F$=0.55 hexane:ethyl acetate 1:1 (v/v);

$^1H$ NMR δ 5.21, 5.09 (2t, 2H, H-3, H-4), 4.94 (t, 1H, H-2), 4.65 (d, 1H, H-1, $J_{1,2}$=8.8 Hz), 4.27, 4.15 (2m, 2H, H-6, H-6'), 3.81 (m, 1H, H-5), 2.09, 2.07, 2.02, 1.99 (4s, 12H, 4Ac);

FAB MS $C_{14}H_{19}N_3O_9$ (373.32) m/z (%) 396 [M+Na]$^+$ (20), 331 [M−N$_3$]$^+$ (100).

Cognate preparation of 2-acetamido-3,4,6-tri-O-acetyl-2-deoxy-β-D-glucopyranosyl azide (8)

$R_F$=0.50 ethyl acetate; yield 87%; $^1H$ NMR δ 5.70 (d, 1H, NH), 5.24 (t, 1H, H-3), 5.09 (t, 1H, H-4), 4.76 (d, 1H, H-1, $J_{1,2}$=9.1 Hz), 4.25, 4.16 (2m, 2H, H-6, H-6'), 3.90 (m, 1H, H-2), 3.79 (m, 1H, H-5), 2.09, 2.03, 2.02, 1.97 (4s, 12H, 4Ac); FAB MS $C_{14}H_{20}N_4O_8$ (372.33) m/z (%) 373 [M+H]$^+$ (100), 395 [M+Na]$^+$ (30), 330 [M−N$_3$]$^+$ (97).

Cognate preparation of O-[2',3',4',6'-tetra-O-acetyl-α-D-gluco-pyranosyl (1'→4)]-2,3,6-tri-O-acetyl-β-D-glucopyranosyl azide (9)

$R_F$=0.30 hexane:ethyl acetate 8:7 (v/v); yield 84%; $^1H$ NMR δ 5.41 (d, 1H, H-1', $J_{1',2'}$=4.0 Hz), 4.85 (dd, 1H, H-4'), 4.78 (t, 1H, H-2), 4.70 (d, 1H, H-1, $J_{1,2}$=8.7 Hz), 2.15-1.99 (7s, 21H, 7Ac); FAB MS $C_{26}H_{35}N_3O_{17}$ (661.57) m/z (%) 684 [M+Na]$^+$ (100), 360 (25).

Cognate preparation of O-{O-[2",3",4",6"-tetra-O-acetyl-α-D-glucopyranosyl(1"→4')]-2',3',6'-tetra-O-acetyl-α-D-gluco-pyranosyl (1'→4)}-1, 2, 3, 6-tetra-O-acetyl-β-D-glucopyranosyl azide (10)

$R_F$=0.70 hexane:ethyl acetate 4:10 (v/v); yield 79%; FAB MS $C_{38}H_{51}N_3O_{25}$ (949.82) m/z (%) 973 [M+Na]$^+$ (100), 945 (38).

Example 2

2,3,4,6-tetra-O-acetyl-β-D-galactopyranosylamine (11)

Palladium catalyst (10% on carbon, 20.0 mg) was added in one portion to a solution of 2,3,4,6-tetra-O-acetyl-β-D- galacto-pyranosyl azide (6)(500 mg, 1.34 mmol) in abs. methanol (5 ml) under a hydrogen atmosphere. A small amount of abs. THF was added to dissolve the sugar. The solution was allowed to stir for 12 hours. The catalyst was subsequently filtered off, and the solvent evaporated. Purification by column chromatography gave (11) (400 mg, 86%).

$R_F$=0.30 hexane:ethyl acetate 8:7 (v/v);. $^1$H NMR δ 5.40 (d, 1H, H-4), 5.04 (m, 2H, H-2, H-3), 4.16 (d, 1H, H-1, $J_{1,2}$=8.0 Hz), 4.10 (m, 2H, H-6, H-6'), 3.99 (m, 1H, H-5), 2.14, 2.07, 2.06, 1.97 (4s, 12H, 4Ac); FAB MS $C_{14}H_{21}NO_9$ (347.32) m/z (%) 370 [M+Na]$^+$ (100).

Cognate preparation of 2,3,4,6-tetra-O-acetyl-β-D-glucopyranosyl-amine (12) from (7)

$R_F$= 0.35 hexane:ethyl acetate 1:1 (v/v); yield 83%; $^1$H NMR δ 5.26 (d, 1H, H-3), 5.16-5.03 (m, 2H, H-2, H-3), 4.12 (d, 1H, H-1, $J_{1,2}$=8.5 Hz), 4.12 (m, 2H, H-6, H-6'), 3.86 (m, 1H, H-5), 2.11, 2.06, 2.04, 2.01 (4s, 12H, 4Ac); FAB MS $C_{14}H_{21}NO_9$ (347.32) m/z (%) 370 [M+Na]$^+$ (80).

Cognate preparation of O-[2',3',4',6'/-tetra-O-acetyl-α-D-gluco-pyranosyl(1→4)]-2,3,6-tri-O-acetyl-β-D-glucopyranosylamine (13) from (9)

$R_F$=0.50 chloroform:ethyl acetate 1:2 (v/v); yield 72%; $^1$H NMR δ 5.43 (d, 1H, H-1'), 4.13 (d, 1H, H-1), 2.14-2.00 (7s, 21H, 7Ac); MALDI TOF MS $C_{26}H_{37}NO_{17}$ (635.57) m/z (%) 659 [M+Na]$^+$ (100), 1278 (43).

Cognate preparation of O-{O-[2",3",4",6"-tetra-O-acetyl-α-D-glucopyranosyl(1'→4')]-2',3',6'-tetra-O-acetyl-β-D-gluco-pyranosyl(1'→4)}-1,2,3,6-tetra-O-acetyl-β-D-glucopyranosylamine (14) from (10)

$R_F$=0.30 hexane:ethyl acetate 6:10 (v/v); yield 66%; FAB MS $C_{38}H_{53}NO_{25}$ (923.82) m/z (%) 925 [M+H]$^+$ (100), 229 (48).

Example 3

2,3,4,6-tetra-O-acetyl-N-{1-(R/S)-[(tert-butoxycarbonyl)amino]-dodecyl}-β-D-glucopyranosylamide (15).

2-(R/S)-[(tert-Butoxycarbonyl)amino]dodecanoic acid (575 mg, 1.44 mmol) and EEDQ (428 mg, 1.72 mmol) were added to a stirred solution of 2,3,4,6-tetra-O-acetyl-β-D-glucopyranosylamine (12) (500 mg, 1.44 mmol) in abs. THF (10 ml). The reaction was stirred at 40° C. for 6 hours. After evaporation, the residue was purified by column chromatography to give (15). $R_F$=0.87 chloroform:methanol 10:2.5 (v/v); yield 68%; $^1$H NMR δ 5.31-5.22 (m, 2H, H-1, H-3), 5.06 (m, 1H, H-4), 4.93 (m, 1H, H-2), 4.79 (br s, 1H, NH), 4.28 (m, 1H, H-6), 4.13-4.05 (m, 2H, H-6', αCH), 3.80 (m, 1H, H-5), 2.06, 2.03, 2.01, 2.00 (4s, 12H, 4Ac), 1.44 (s, 9H, 3×Boc CH$_3$), 1.28-1.23 (m, 18H, 9CH$_2$), 0.87 (t, 3H, CH$_3$); FAB MS $C_{31}H_{52}N_2O_{12}$ (644.75) m/z (%) 667 [M+Na]$^+$ (10), 777 [M+Cs]$^+$ (100), 545 [M−Boc+H]$^+$ (15).

Cognate preparation of 2,3,4,6-tetra-O-acetyl-N-{1-(R/S)-[(tert-butoxycarbonyl)amino]tetradecyl}-β-D-glucopyranosylamide (16) from (12) and 2-(R/S)-[(tert-butoxycarbonyl)amino]tetradecanoic acid $R_F$=0.42 hexane:ethyl acetate 1:1 (v/v); yield 64%; $^1$H NMR δ 5.28 (m, 2H, H-1, H-3), 5.06 (m, 1H, H-4), 4.97 (m, 2H, H-2, NH), 4.26, 4.11 (2m, 2H, H-6, H-6'), 3.83 (m, 1H, H-5), 2.08, 2.04, 2.02, 1.99 (4s, 12H, 4Ac), 1.42 (s, 9H, 3×Boc CH$_3$), 1.25 (m, 22H, 11CH$_2$), 0.86 (t, 3H, CH$_3$); FAB MS $C_{33}H_{56}N_2O_{12}$ (672.80) m/z (%) 695 [M+Na]$^+$ (40), 805 [M+Cs]$^+$ (65), 573 [M−Boc+H]$^+$ (95).

Cognate preparation of 2,3,4,6-tetra-O-acetyl-N-{1-(R/S)-[(tert-butoxycarbonyl)amino]octadecyl}-β-D-glucopyranosylamide (17) from (12) and 2-(R/S)-[(tert-butoxycarbonyl)amino]hexadecanoic acid $R_F$=0.34 hexane:ethyl acetate 2:1 (v/v); yield 70%; $^1$H NMR δ 6.75 (d, 1H, NH), 5.25 (m, 2H, H-1, H-3), 5.07 (dd, 1H, H-4), 4.94 (dd, 1H, H-2), 4.78 (s, 1H, NHC=O), 4.22, 4.06 (2m, 2H, H-6, H-6'), 3.98 (m, 1H, αCH), 3.80 (m, 1H, H-5), 2.07, 2.04, 2.02, 2.00 (4s, 12H, 4Ac), 1.44 (s, 9H, 3×Boc CH$_3$), 1.24 (m, 30H, 15CH$_2$), 0.88 (t, 3H, CH$_3$); FAB MS $C_{37}H_{64}N_2O_{12}$ (728.91) m/z (%) 751 [M+Na]$^+$ (33), 861 [M+Cs]$^+$ (27), 629 [M−Boc+H]$^+$ (75).

Cognate preparation of 2,3,4,6-tetra-O-acetyl-N-{1-(R/S)-[(tert-butoxycarbonyl)amino]dodecyl}-β-D-galactopyranosylamide (18) from (11) and 2-(R/S)-[(tert-butoxycarbonyl)amino]dodecanoic acid $R_F$=0.54 chloroform:methanol 10:0.2 (v/v); yield 66%; $^1$H NMR δ 5.52 (d, 1H, H-4), 5.16 (m, 3H, H-1, H-2, H-3), 4.75 (br, 1H, NH), 4.21, 4.09 (2m, 4H, αCH, H-5, H-6, H-6'), 2.19, 2.06, 2.03, 1.99 (4s, 12H, 4Ac), 1.45 (s, 9H, 3×Boc CH$_3$), 1.26 (m, 18H, 9CH$_2$), 0.88 (t, 3H, CH$_3$); FAB MS $C_{31}H_{52}N_2O_{12}$ (644.75) m/z (%) 667 [M+Na]$^+$ (65), 544 [M−Boc+H]$^+$ (55), 331 (40).

Cognate preparation of 2,3,4,6-tetra-O-acetyl-N-{1-(R/S)-[(tert-butoxycarbonyl)amino]tetradecyl}-β-D-galactopyranosylamide (19) from (11) and 2-(R/S)-[(tert-butoxycarbonyl)amino]tetradecanoic acid $R_F$=0.38 hexane:ethyl acetate 1:1 (v/v); yield 69%; $^1$H NMR δ 5.53 (m, 1H, H-4), 5.25-5.13 (m, 3H, H-1, H-2, H-3), 4.20-4.11 (m, 4H, αCH, H-5, H-6, H-6'), 2.17, 2.04, 2.03, 2.00 (4s, 12H, 4Ac), 1.43 (s, 9H, 3×Boc CH$_3$), 1.26 (m, 22H, 11CH$_2$), 0.87 (t, 3H, CH$_3$); FAB MS $C_{33}H_{56}N_2O_{12}$ (672.80) m/z (%) 695 [M+Na]$^+$ (25), 573 [M-Boc+H]$^+$ (100).

Cognate preparation of 2,3,4,6-tetra-O-acetyl-N-{1-(R/S)-[(tert-butoxycarbonyl)amino]hexadecyl}-β-D-galactopyranosylamide (20) from (11) and 2-(R/S)-[(tert-butoxycarbonyl)amino]hexadecanoic acid $R_F$=0.40 ethyl acetate; yield 66%; $^1$H NMR δ 5.43 (d, 1H, H-4), 5.22 (m, 1H, H-3), 5.12 (m, 2H, H-1, H-2), 4.80 (br s, 1H, NH), 4.09 (m, 3H, (αCH, H-6, H-6'), 4.02 (m, 1H, H-5), 2.17, 2.03, 1.99 (3s, 12H, 4Ac), 1.46, 1.44 (2s, 9H, 3×Boc CH$_3$), 1.35-1.22 (m, 26H, 13CH$_2$), 0.88 (t, 3H, CH$_3$);
MALDI TOF MS $C_{35}H_{60}N_2O_{12}$ (700.86) m/z (%) 724 [M+Na]$^+$ (100), 602 [M−Boc+H]$^+$ (51).

Cognate preparation of O-[2',3',4',6'-tetra-O-acetyl-α-D-gluco-pyranosyl(1'→4)]-2,3,6-tri-O-acetyl-N-{1-(R/S)-[(tert-butoxy-carbonyl)amino]octadecyl}-α-D-glucopyranosylamide (23) from (13) and 2-(R/S)-[(tert-butoxycarbonyl)amino]octadecanoic acid $R_F$=0.56 chloroform:methanol 10:0.3 (v/v); yield 64%; $^1$H NMR δ 5.40-5.22 (m, 4H), 5.05 (t, 1H), 4.86 (m, 1H), 4.77 (m, 1H), 4.39 (m, 1H), 4.22 (m, 2H), 4.02 (m, 2H), 3.94 (m, 2H), 3.78 (m, 1H), 2.12-1.99 (7s, 21H, 7Ac), 1.70 (m, 2H, αCH$_2$), 1.44, 1.43 (2s, 9H, 3×Boc CH$_3$), 1.25 (m, 28H, 14CH$_2$), 0.87 (t, 3H, CH$_3$); Anal. Calcd. for C$_{49}$H$_{80}$N$_2$O$_{20}$ (1017.16): C, 57.87; H, 7.87; N, 2.75. Found C, 57.72; H, 7.91; N, 2.81; FAB MS (1017.16) m/z (%) 1039 [M+Na]$^+$ (97), 918 (100).

Cognate preparation of O-{O-[2",3",4",6"-tetra-O-acetyl-α-D-glucopyranosyl(1"→4')]-2',3',6'-tetra-O-acetyl-α-D-gluco-pyranosyl(1'→4)}-1,2,3,6-tetra-O-acetyl-N-{1-(R/S)-[(tert-butoxy-carbonyl)amino]octadecyl}-β-D-glucopyranosylamide (24) from (14) and 2-(R/S)-[(tert-Butoxycarbonyl)amino]octadecanoic acid.

$R_F$=0.11 chloroform:methanol 10:0.2 (v/v); yield, 53%; $^1$H NMR δ 5.40-5.33 (m, 4H), 5.25 (m, 2H), 5.06 (dd, 1H), 4.90 (dd, 1H), 4.76 (m, 2H), 4.43 (m, 1H), 4.23 (m, 2H), 4.16 (d, 1H), 4.06 (dd, 1H), 3.94 (m, 5H), 3.82 (m, 1H), 2.15-1.99 (10s, 30H, 10Ac), 1.70 (m, 2H, βCH$_2$), 1.44, 1.43 (2s, 9H, 3×Boc CH$_3$), 1.25 (m, 28H, 14CH$_2$), 0.88 (t, 3H, CH$_3$);

Anal. Calcd. for C$_{49}$H$_{80}$N$_2$O$_{20}$ (1305.41): C, 56.13; H, 7.36; N, 2.15. Found C, 56.02; H, 7.42; N, 2.19; FAB MS (1305.41) m/z (%) 1328 [M+Na]$^+$ (28), 1438 [M+Cs]$^+$ (18), 439 (10).

Example 4

2-acetamido-3,4,6-tri-O-acetyl-2-deoxy-N-{1-(R/S)-[(tert-butoxy-carbonyl)amino]-tetradecyl}-β-D-glucopyranosylamide (21)

Tributyl-n-phosphine (4.88 g, 24.2 mmol) was dissolved in abs. CH$_2$Cl$_2$ (50 ml) and added dropwise to a stirred solution of 2-acetamido-3,4,6-tri-O-acetyl-2-deoxy-β-D-glucopyranosyl azide (8) (6.00 g, 16.1 mmol) and 2-(R/S)-[(tert-butoxycarbonyl)amino]-tetradecanoic acid (10.2 g, 32.3 mmol) in abs. CH$_2$Cl$_2$ (100 ml) over 20 minutes. After stirring for 2 hours at room temperature, the reaction mixture was diluted with CH$_2$Cl$_2$ (100 ml) and washed with Na HCO$_{3(sat, aq)}$ (2×100 ml). The organic phase was dried over MgSO$_4$, filtered and evaporated. The product was purified by column chromatography in chloroform:methanol 10:0.2 (v/v) to give (21) (8.50 g, 82%).

$R_F$=0.64 hexane:ethyl acetate 1:3 (v/v); $^1$H NMR δ 5.11, 5.01 (2m, 2H, H-3, H-4), 4.45 (d, 1H, H-1, J$_{1,2}$=9.5 Hz), 4.21, 4.10 (2m, 3H, αCH, H-6, H-6'), 3.81-3.65 (m, 2H, H-2, H-5), 2.06, 2.05, 2.00, 1.97 (3s, 12H, 4Ac), 1.43 (s, 9H, 3×Boc CH$_3$), 1.25 (m, 22H, 11CH$_2$), 0.86 (t, 3H, CH$_3$); FAB MS C$_{33}$H$_{57}$N$_3$O$_{11}$ (671.82) m/z (%) 694 [M+Na]$^+$ (45), 572 [M−Boc+H]$^+$ (100).

Cognate preparation of 2-acetamido-3,4,6-tri-O-acetyl-2-deoxy-N-{1-(R/S)-[(tert-butoxycarbonyl)amino]-dodecyl}-β-D-glucopyranosyl-amide (22) from (8) and 2-(R/S)-[(tert-butoxycarbonyl)amino]-dodecanoic acid.

$R_F$=0.64 chloroform:methanol 10:0.7 (v/v); yield 76%; $^1$H NMR δ 5.09-4.98 (m, 2H, H-3, H-4), 4.41 (d, 1H, H-1, J$_{1,2}$=9.6 Hz), 4.20-4.08 (m, 3H, αCH, H-6, H-6'), 3.68 (m, 2H, H-2, H-5), 2.07, 1.99, 1.96 (3s, 12H, 4Ac), 1.44 (s, 9H, 3×Boc CH$_3$), 1.26 (m, 18H, 9CH$_2$), 0.87 (t, 3H, CH$_3$); FAB MS C$_{31}$H$_{53}$N$_3$O$_{11}$ (643.77) m/z (%) 644 [M+H]$^+$ (40), 544 [M−Boc+H]$^+$ (100).

Example 5

N-{1-(R/S)-[(tert-Butoxycarbonyl)amino]dodecyl}-β-D-glucopyranosyl-amide (25) from (15)

2,3,4,6-tetra-O-acetyl-N-{1-(R/S)-[(tert-butoxycarbonyl)-amino]dodecyl}-β-D-glucopyranosylamide (15) (4.00 g, 6.182 mmol) was dissolved in abs. methanol (40 ml). Sodium methoxide was added (0.5M, 0.618 mmol) and the reaction was stirred for 3 hours. The reaction was neutralised with Amberlite H$^+$ ion exchange resin. The solution was then filtered and the resin washed with methanol.

$R_F$=0.51 chloroform:methanol 10:2.5 (v/v); yield 87%; $^1$H NMR δ 4.86 (d, 1H, H-1, J$_{1,2}$=9.3 Hz), 3.98 (m, 1H, αCH), 3.79, 3.62 (2m, 2H, H-6, H-6'), 3.37-3.21 (m, 4H), 1.41 (s, 9H, 3×Boc CH$_3$), 1.26 (m, 18H, 9CH$_2$), 0.87 (t, 3H, CH$_3$); FAB MS C$_{23}$H$_{44}$N$_2$O$_8$ (476.60) m/z (%) 477 [M+H]$^+$ (3), 499 [M+Na]$^+$ (80), 377 [M−Boc+H]$^+$ (10).

Cognate preparation of N-{1-(R/S)-[(tert-butoxycarbonyl)amino]-dodecyl}-β-D-galactopyranosylamide (26) from (18)

$R_F$=0.28 chloroform:methanol 10:2 (v/v); yield 85%; $^1$H NMR δ 5.49 (d, 1H, NH), 4.87 (m, 1H, H-1), 4.10-3.95 (m, 1H, αCH), 3.89 (d, 1H, H-4), 3.70-3.51 (3m, 5H, H-2, H-3, H-5, H-6, H-6'), 1.45 (s, 9H, 3×Boc CH$_3$), 1.29 (m, 18H, 9CH$_2$), 0.90 (t, 3H, CH$_3$); FAB MS C$_{23}$H$_{44}$N$_2$O$_8$ (476.60) m/z (%) 499 [M+Na]$^+$ (35), 399 [M−Boc+H]$^+$ (90).

Cognate preparation of 2-acetamido-2-deoxy-N-{1-(R/S)-[(tert-butoxycarbonyl)amino]dodecyl}-β-D-glucopyranosyl amide (27) from (22)

$R_F$=0.39 chloroform:methanol 10:2 (v/v); yield 87%; $^1$H NMR 67, 3.86-3.38 (m, 8H), 1.41 (s, 9H, 3×Boc CH$_3$), 1.28-1.21 (m, 18H, 9CH$_2$), 0.86 (t, 3H, CH$_3$); FAB MS C$_{25}$H$_{47}$N$_3$O8 (517.66) m/z (%) 518 [M+H]$^+$ (40), 540 [M+Na]$^+$ (50).

Example 6

N-(2-amino-(R/S)-dodecoyl)-O-D-glucopyranosylamine (30)

Residue (25) (1.34 g, 2.82 mmol) was dissolved in CH$_2$Cl$_2$:TFA 1:1 (v/v) (6 ml) and stirred at room temperature for 15 minutes. The solvent was evaporated and co-evaporated with toluene to give (30) (860 mg, 81%).

$R_F$=0.05 chloroform:methanol 10:2 (v/v); $^1$H NMR δ 4.88-3.30 (m, 8H), 1.28-1.16 (m, 18H, 9CH$_2$), 0.78 (t, 3H, CH$_3$); FAB MS C$_{18}$H$_{36}$N$_2$O$_6$ (376.49) m/z (%) 377 [M+H]$^+$ (10), 399 [M+Na]$^+$ (30).

Cognate preparation of N-(1-amino-(R/S)-dodecoyl)-β-D-galacto-pyranosylamine (31) from (26).

$R_F$=0.05 chloroform:methanol 10:2 (v/v); yield 97%; $^1$H NMR δ 4.20-3.24 (m, 8H), 1.38-1.16 (m, 18H, 9CH$_2$), 0.78 (t, 3H, CH$_3$); FAB MS C$_{18}$H$_{36}$N$_2$O$_6$ (376.49) m/z (%) 399 [M+Na]$^+$ (60).

Cognate preparation of 2-acetamido-2-deoxy-N-(1-amino-(R/S)-dodecoyl)-β-D-glucopyranosylamine (32) from (27).

$R_F$=0.05 chloroform:methanol 10:2 (v/v); yield 95%; $^1$H NMR δ 7.35 (m, 1H, NH), 4.91 (m, 1H, H-1), 3.94-3.31 (m, 8H), 1.28-1.20 (m, 18H, 9CH$_2$), 0.82 (t, 3H, CH$_3$); FAB MS C$_{20}$H$_{39}$N$_3$O$_6$ (417.54) m/z (%) 418 [M+H]$^+$ (3), 440 [M+Na]$^+$ (5).

Cognate preparation of O-[α-D-glucopyranosyl (1'→4)]-N-{1-amino-(R/S)-octadecoyl}-β-D-glucopyranosylamine (33)

De-O-protection of 23 was effected using the procedure described in experiment 5 to give 28, which was subsequently de-N-protected, using the procedure described above to give 33.

$R_F$=0.31 chloroform:methanol 1:1 (v/v); yield 81%; $^1$H NMR (CD$_3$OD) δ 5.18-4.96 (m, 2H), 3.88-3.42 (m, 12H), 1.28 (m, 30H, 15CH$_2$), 0.88 (t, 3H, CH$_3$); Anal. Calcd. for C$_{30}$H$_{58}$N$_2$O$_{11}$ (622.40): C, 57.87; H, 9.32; N, 4.50. Found C, 57.82; H, 9.37; N, 4.44; FAB MS (622.40) m/z (%) 623 [M+H]$^+$ (3), 645 [M+Na]$^+$ (6), 307 (100); HRMS Calcd. for C$_{30}$H$_{58}$N$_2$11: 623.4119. Found 623.4110.

Cognate preparation of O-{O-[α-D-glucopyranosyl (1"→4')]-α-D-gluco-pyranosyl (1'→4)}-N-{1-amino-(R/S)-octadecoyl}-β-D-glucopyranosylamine (34)

De-O-protection of 24 was effected using the procedure described in experiment 5 to give 29, which was subsequently de-N-protected, using the procedure described above to give 34. $R_F$=0.39 chloroform:methanol 3:2 (v/v); yield 75%; $^1$H NMR (CD$_3$OD) δ 5.08 (m, 3H), 3.90-3.37 (m, 18H), 1.29 (m, 30H, 15CH$_2$), 0.89 (t, 3H, CH$_3$); Anal. Calcd. for C$_{36}$H$_{68}$N$_2$O$_{16}$ (784.46): C, 55.10; H, 8.67; N, 3.57. Found C, 55.33; H, 8.44; N, 3.63; FAB MS (784.46) m/z (%) 785 [M+H]$^+$ (50), 807 [M+Na]$^+$ (100); HRMS Calcd. for C$_{36}$H$_{68}$N$_2$O$_{16}$Na: 807.4467. Found 807.4460.

Example 7

Piperacillin/2-acetamido-2-deoxy-N-(1-amino-(R/S)-dodecoyl)-β-D-gluco-pyranosylamine Ionic Complex (35)

Piperacillin (2.00 g, 3.87 mmol) and 2-acetamido-2-deoxy-N-(1-amino-(R/S)-dodecoyl)-β-D-glucopyranosylamine (32) (1.61 g, 3.87 mmol) were dissolved in 95% acetic acid. Once fully dissolved, the solution was filtered and lyophilised to give (35) as a white solid (3.50 g, 97%).

RP-HPLC: $R_t$=12.46 min. ESI MS [M (complex 35)=934; M$^1$ (glycolipid 32)=417] m/z (%) 935 [M+H]$^+$ (100), 418 [M$^1$+H]$^+$ (45).

Example 8

Preparation of Glycosyl Halides 2,3,4,6-tetra-O-acetyl-α-D-galactopyranosyl bromide (36)

Acetic anhydride (1 ml) was added to HBr in acetic acid (45%, 12 ml) and allowed to stir for 30 minutes. 1,2,3,4,6-penta-O-acetyl-α/β-D-galactopyranose 6 (6.00 g, 15.4 mmol) was then dissolved in a minimal quantity of absolute CH$_2$Cl$_2$, added to the solution and stirred for 2 hours. The reaction mixture was then diluted with CH$_2$Cl$_2$ (cold, −15° C., 100 ml), washed with water (3×300 ml) and Na HCO$_{3\ (sat,\ aq)}$ (1×300 ml). The organic phase was dried over MgSO$_4$, filtered and evaporated. Purification by column chromatography gave 19 (6.05 g, 96%).

$R_F$=0.52 hexane:ethyl acetate 1:2 (v/v); $^1$H NMR δ 6.71 (d, 1H, H-1, $J_{1,2}$=3.5 Hz), 5.52 (d, 1H, H-4), 5.42 (dd, 1H, H-3), 5.03 (dd, 1H, H-2), 4.50 (t, 1H, H-6'), 4.16 (m, 2H, H-6, H-5); FAB MS C$_{14}$H$_{19}$BrO$_9$ (411.20) m/z (%) 433, 435 [M+Na]$^+$ (17, 16), 543, 545 [M+Cs]$^+$ (67, 65), 331 [M−Br]$^+$ (100).

Cognate preparation of 2,3,4,6-tetra-O-acetyl-α-D-glucopyranosyl bromide (37)

$R_F$=0.61 hexane:ethyl acetate 1:1 (v/v); yield 93%; $^1$H NMR δ 6.52 (d, 1H, H-1, $J_{1,2}$=3.6 Hz), 5.46 (d, 1H, H-3), 5.38 (dd, 1H, H-4), 4.94 (dd, 1H, H-2), 4.44 (t, 1H, H-6'), 4.12 (m, 2H, H-6, H-5), 2.15, 2.10, 2.05, 1.97 (4s, 12H, 4Ac); FAB MS C$_{14}$H$_{19}$BrO$_9$ (411.20) m/z (%) 433, 435 [M+Na]$^+$ (34, 31), 543, 545 [M+Cs]$^+$ (71, 69), 331 [M−Br]$^+$ (80).

Cognate preparation of 2,3,4,6-tetra-O-acetyl-α-D-mannopyranosyl bromide (38)

$R_F$=0.35 hexane:ethyl acetate 1:1 (v/v); yield 91%; $^1$H NMR δ 6.27 (d, 1H, H-1, $J_{1,2}$=1.4 Hz), 5.66 (dd, 1H, H-3), 5.35 (dd, 1H, H-2), 5.27 (m, 1H, H-4), 4.25 (m, 1H, H-6'), 4.12, 4.07 (2m, 2H, H-6, H-5), 2.17, 2.11, 2.06, 2.01 (4s, 12H, 4Ac); FAB MS C$_{14}$H$_{19}$BrO$_9$ (411.20) m/z (%) 411, 412 [M+H]$^+$ (30, 30), 433, 435 [M+Na]$^+$ (29, 29), 331 [M−Br]$^+$ (100).

Preparation of 2-acetamido-3,4,6-tri-O-acetyl-2-deoxy-α-D-gluco-pyranosyl chloride (39)

2-acetamido-2-deoxy-α-D-glucopyranose (15.0 g, 67.8 mmol) was suspended in acetyl chloride (65 ml) and stirred at 45° C. for 12 hours. The acetyl chloride was then removed by evaporation and co-evaporation with toluene and benzene. The product was purified by column chromatography using chloroform:ethyl acetate 10:4 (v/v) to give 39 (15.9 g, 64%).

$R_F$=0.65 hexane:ethyl acetate 1:4 (v/v); $^1$H NMR δ 6.17 (d, 1H, H-1, $J_{1,2}$=3.6 Hz), 5.88 (d, 1H, NH), 5.29 (t, 1H, H-3), 5.20 (m, 1H, H-4), 4.50 (m, 1H, H-2), 4.25, 4.10 (2m, 3H, H-6, H-6', H-5), 2.09, 2.03, 2.02, 1.97 (4s, 12H, 4Ac); FAB MS $C_{14}H_{20}ClNO_8$ (365.76) m/z (%) 366 [M+H]$^+$ (100), 388 [M+Na]$^+$ (75), 331 [M−Cl]$^+$ (18).

Example 9

Preparation of Lipoamino Acids 2-(R/S)-[(tert-Butoxycarbonyl)amino]dodecanoic acid (40)

Diethyl acetamidomalonate (81.3 g, 0.375 mol) was added to a stirred solution of sodium (8.40 g, 0.365 mol) in abs. ethanol (300 ml). 1-bromodecane (110 g, 0.498 mol, 105 ml) was then added to the solution. The reaction mixture was refluxed for 24 hours. After evaporation of the solvent, the oily residue was taken up in ethyl acetate (500 ml) and washed with water (1×500 ml) and brine (1×500 ml). The solution was then dried over MgSO$_4$, filtered and evaporated. The resulting oil was dissolved in concentrated hydrochloric acid (600 ml) and DMF (70 ml) and refluxed for 48 hours. On completion, the reaction mixture was poured onto ethanol:water 3:1 (750 ml). A solid product was precipitated from ammonia, filtered off and washed with ether (2×100 ml). The solid lipoamino acid [2-(R/S)-aminododecanoic acid] was then suspended in tert-butanol:water 2:3 (900 ml) and the pH corrected to 11. Di-tert-butyl dicarbonate (101 g, 0.463 mol) was then added to the solution, which was subsequently stirred for 48 hours. The solution was diluted with water (360 ml) and made pH 3 by addition of potassium hydrogensulphate. The product was extracted into ethyl acetate (500 ml) and was washed with brine (1×500 ml). The solution was then dried over MgSO$_4$, filtered and evaporated. Re-crystallisation from acetonitrile gave 40 (96.2 g, 82%).

$R_F$=0.41 hexane:ethyl acetate 4:1 (v/v); $^1$H NMR δ 4.99 (s, 1H, NH), 4.30 (m, 1H, αCH), 1.42 (s, 9H, 3×Boc CH$_3$), 1.20-1.29 (m, 18H, 9CH$_2$), 0.86 (t, 3H, CH$_3$); FAB MS $C_{17}H_{33}O_4N$ (315.45) m/z (%) 316 [M+H]$^+$ (27), 338 [M+Na]$^+$ (95), 216 [M−Boc+H]$^+$ (68).

Cognate preparation of
2-(R/S)-[(tert-Butoxycarbonyl)amino]-tetradecanoic acid (41)

$R_F$=0.26 hexane:ethyl acetate 4:1 (v/v); yield 68%; $^1$H NMR δ 5.00 (s, 1H, NH), 4.28 (m, 1H, αCH), 1.40 (s, 9H, 3×Boc CH$_3$), 1.24 (m, 22H, 11CH$_2$), 0.87 (t, 3H, CH$_3$); FAB MS $C_{19}H_{37}O_4N$ (343.50) m/z (%) 344 [M+H]$^+$ (20), 366 [M+Na]$^+$ (80), 243 [M−Boc+H]$^+$ (75).

Cognate preparation of
2-(R/S)-[(tert-Butoxycarbonyl)amino]-hexadecanoic acid (42)

$R_F$=0.41 hexane:ethyl acetate 4:1 (v/v); $^1$H NMR δ 4.32 (m, 1H, αCH), 1.43 (s, 9H, 3×Boc CH$_3$), 1.22 (m, 26H, 13CH$_2$), 0.86 (t, 3H, CH$_3$); FAB MS $C_{21}H_{41}O_4N$ (371.55) m/z (%) 372 [M+H]$^+$ (27), 394 [M+Na]$^+$ (70), 272 [M−Boc+H]$^+$ (40).

Cognate preparation of
2-(R/S)-[(tert-Butoxycarbonyl)amino]-octadecanoic acid (43)

$R_F$=0.39 hexane:ethyl acetate 4:1 (v/v); $^1$H NMR δ 5.01 (m, 1H, NH), 4.28 (m, 1H, αCH), 1.42 (s, 9H, 3×Boc CH$_3$), 1.23 (m, 28H, 15CH$_2$), 0.87 (t, 3H, CH$_3$); FAB MS $C_{23}H_{45}O_4N$ (399.61) m/z (%) 400 [M+H]$^+$ (37), 422 [M+Na]$^+$ (20), 300 [M−Boc+H]$^+$ (80).

Example 10

Preparation of Lipoamino Alcohols tert-Butyl N-[1-(R/S)-(hydroxymethyl)tridecyl]carbamate (44)

2-(R/S)-[(tert-butoxycarbonyl)amino]tetradecanoic acid 41 (1.00 g, 2.92 mmol) in abs. THF (3 ml) was added slowly dropwise to BH$_3$-THF complex (1.0M, 5.8 ml, 5.80 mmol) at 0° C. After stirring for 2 hours, the reaction mixture was quenched with 10% acetic acid in methanol (v/v) and evaporated. The residue was taken up in CH$_2$Cl$_2$ (10 ml) and washed with 1M KHSO$_{4(aq)}$ (1×20 ml) and brine (2×20 ml). The solution was then dried over MgSO$_4$, filtered and evaporated. Purification by column chromatography gave 44 (821 mg, 86%).

$R_F$=0.82 chloroform:methanol 10:1 (v/v); $^1$H NMR δ 3.72-3.48 (m, 3H, αCH, CH$_2$), 1.40 (s, 9H, 3.x Boc CH$_3$), 1.25 (m, 22H, 11CH$_2$), 0.86 (t, 3H, CH$_3$); FAB MS $C_{19}H_{39}NO_3$ (329.52) m/z (%) 330 [M+H]$^+$ (6), 352 [M+Na]$^+$ (10), 462 [M+Cs]$^+$ (8), 230 [M−Boc+H]$^+$ (100).

Cognate preparation of tert-butyl
N-[1-(R/S)-(hydroxymethyl) pentadecyl]carbamate (45)

Procedure as for 44, Method C (using 42 in place of 41). $R_F$=0.72 chloroform:methanol 10:0.7 (v/v); yield 82%; $^1$H NMR δ 3.69-3.45 (m, 2H, αCH, CH$_2$a), 2.97 (m, 1H, CH$_2$b), 1.41 (s, 9H, 3×Boc CH$_3$), 1.25 (m, 18H, 13CH$_2$), 0.88 (t, 3H, CH$_3$); FAB MS $C_{21}H_{43}NO_3$ (357.32) m/z (%) 380 [M+Na]$^+$ (15), 258 [M−Boc+H]$^+$ (100).

Cognate preparation of tert-butyl
N-[1-(R/S)-(hydroxymethyl) undecyl]carbamate (46)

Procedure as for 44 (using 40 in place of 41). $R_F$=0.50 hexane:ethyl acetate 4:1 (v/v); yield 87%; $^1$H NMR δ 3.65-3.48 (m, 3H, αCH, CH$_2$), 1.43 (s, 9H, 3×Boc CH$_3$), 1.24 (m, 18H, 9CH$_2$), 0.86 (t, 3H, CH$_3$); FAB MS $C_{17}H_{35}NO_3$ (301.46) m/z (%) 302 [M+H]$^+$ (15), 324 [M+Na]$^+$ (5), 434 [M+Cs]$^+$ (10), 202 [M−Boc+H]$^+$ (95).

Example 11

Preparation of O-Linked Sugar-Lipids

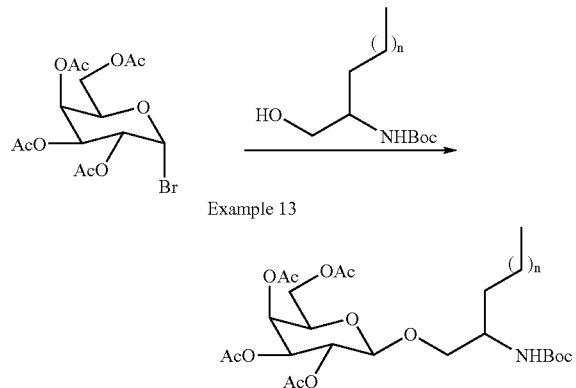

Example 13

2,3,4,6-tetra-O-acetyl-α-D-galactopyranosyl bromide 36 (10 gm) is dissolved in anhydrous dichloroethane (150 mL) and to this solution is added freshly activated 4A molecular sieves (10 gm). The resultant solution is stirred under nitrogen and tert-butyl N-[1-(R/S)-(hydroxymethyl)undecyl]carbamate (9a) (9.5 gm, 1.3 eq) is added. Finally, silver trifluoromethanesulfonate (10 gm) is added and the reaction mixture stirred at room temperature for 2 hours. After this time the solution is filtered through a pad of celite, and the solution extracted with 2 times 100 mL of saturated sodium chloride solution then dried over magnesium sulfate. The solution is filtered, evaporated to dryness and chromatographed on silica (hexane:ethyl acetate 2:1) to yield the β glycoside as the major product.

Reaction with other aminoalcohols and other glycosyl halides proceeds in a similar manner, with the exception of 2-acetamido-3,4,6-tri-O-acetyl-2-deoxy-α-D-glucopyranosyl chloride (39), which did not yield the desired product. An alternative procedure for this material via the trichloroacetimidate is described below.

1,3,4,6-Tetra-O-acetyl-2-deoxy-2-(2,2,2-trichloroethoxycarbonyl-amino)-α/β-D-glucopyranose (47)

2,2,2-Trichloroethoxycarbonyl chloride (Troc-Cl) (12.7 g, 59.9 mmol) was added dropwise at room temperature to a vigorously stirred solution of α-D-glucosamine hydrochloride and NaHCO$_3$ (12.6 g, 150 mmol) in water (150 ml). The solution was stirred for 1 hour. The reaction mixture was then neutralised with 1M HCl (50 ml) and evaporated. The residue was dissolved in pyridine (50 ml) and acetic anhydride (25 ml) and was stirred for 12 hours. Following evaporation, the residue dissolved in CH$_2$Cl$_2$ (200 ml) and was washed with 1M HCl$_{(aq)}$ (1×200 ml), water (1×200 ml) and sat. NaHCO$_3$ (1×200 ml). The organic phase was dried over MgSO$_4$, filtered and evaporated to give 47 (22.6 g, 72%) as white foamy crystalline material.

R$_F$=0.31 hexane:ethyl acetate 1:1 (v/v); $^1$H NMR δ 6.22 (d, 1H, NH), 5.27-5.16 (m, 3H, H-1, H-3, H-4), 4.80, 4.60 (2d, 2H, Cl$_3$CCH$_2$), 4.27-4.10 (m, 2H, H-2, H-6), 4.06-3.90 (m, 2H, H-5, H-6'), 2.19, 2.10, 2.03, 2.02 (4s, 12H, 4Ac); FAB MS C$_{17}$H$_{22}$Cl$_3$NO$_{11}$ (522.71) m/z (%) 546 [M+Na]$^+$ (18), 462 [M−OAc]$_+$ (43).

3,4,6-Tri-O-acetyl-2-deoxy-2-(2,2,2-trichloroethoxy-carbonylamino)-α/β-D-glucopyranose (48)

1,3,4,6-tetra-O-acetyl-2-deoxy-2-(2,2,2-trichloroethoxy-carbonylamino)-α/β-D-glucopyranose 47 (3.10 g, 5.99 mmol) and hydrazine acetate (660 mg, 7.17 mmol) were stirred in abs. DMF (30 ml) at room temperature for 40 minutes. Following evaporation, the residue dissolved in CH$_2$Cl$_2$ (80 ml) and was washed with brine (1×50 ml) and water (1×30 ml). The solution was dried over MgSO$_4$, filtered and evaporated to give 48 (2.80 g, crude), which was used in the next reaction without further purification.

R$_F$=0.25 hexane:ethyl acetate 1:1 (v/v); $^1$H NMR δ 5.35-5.31 (m, 2H, H-1, H-4), 5.12 (t, 1H, H-3), 4.80, 4.63 (2d, 2H, Cl$_3$CCH$_2$), 4.23-4.19 (m, 2H, H-2, H-6), 4.15-4.00 (m, 2H, H-5, H-6'), 2.09, 2.03, 2.00 (3s, 9H, 3Ac); FAB MS C$_{15}$H$_{20}$Cl$_3$NO$_{10}$ (480.68) m/z (%) 502 [M+Na]$^+$ (17), 464 [M−OH]$^+$ (48), 302 [M−troc+H]$^+$ (93). O-[3,4,6-Tri-O-acetyl-2-deoxy-2-(2,2,2-trichloroethoxycarbonyl-amino)-α/β-D-glucopyranosyl]trichloroacetimidate (49)

Sodium hydride (0.32 g, 8.10 mmol) was added to a mixture of 3,4,6-tri-O-acetyl-2-deoxy-2-(2,2,2-trichloroethoxycarbonylamino)-α/β-D-glucopyranose 48 (2.80 g, 5.83 mmol), trichloroacetonitrile (5.05 g, 34.9 mmol) and molecular sieves (500 mg) at 0° C. The reaction was then stirred for 2 hours at room temperature. The solution was subsequently filtered through a celite pad, evaporated and the residue was purified by column chromatography in hexane:ethyl acetate 6:4 (v/v) to give 49 (1.70 g, 47%).

R$_F$=0.46 hexane:ethyl acetate 1:1 (v/v); $^1$H NMR δ 6.42 (m, 1H, H-1, J$_{1,2}$=3.2 Hz), 5.35-5.20 (m, 3H, H-3, H-4, NH), 4.70 (d, 2H, Cl$_3$CCH$_2$), 4.29-4.25 (m, 2H, H-2, H-6), 4.15-4.10 (m, 2H, H-5, H-6'), 2.09, 2.05, 2.03 (3s, 9H, 3Ac); FAB MS C$_{17}$H$_{20}$Cl$_6$N$_2$O$_{10}$ (625.06) m/z (%) 648 [M+Na]$^+$ (8), 461 [M−OC(NH)CCl$_3$]$^+$ (44), 301 [M−troc+H]$^+$ (100).

tert-Butyl 1-{[3,4,6-tri-O-acetyl-2-deoxy-2-(2,2,2-trichloroethoxy-carbonylamino)-β-D-glucopyranosyloxy]methyl}-(R/S)-undecylcarbamate (50)

O-[3,4,6-tri-O-acetyl-2-deoxy-2-(2,2,2-trichloroethoxy-carbonylamino)-α-D-gluco-pyranosyl]trichloroacetimidate 49 (125 mg, 0.20 mmol), tert-butyl N-[1-(R/S)-(hydroxymethyl)undecyl]-carbamate 46 (45.0 mg, 0.150 mmol) and molecular sieves (200 mg) were stirred in abs. CH$_2$Cl$_2$ (5 ml) for 15 minutes. Boron trifluoride etherate (64.0 mg, 0.451 mmol) in abs. CH$_2$Cl$_2$ (3 ml) was added dropwise at 0° C. over 20 minutes. The mixture was stirred for 2 hours at room temperature. The reaction mixture was then diluted with CH$_2$Cl$_2$ (10 ml) and filtered through a Celite pad. The solution was washed with NaHCO$_{3(sat, aq)}$ (1×10 ml) and water (1×10 ml). The organic layer was dried over MgSO$_4$, filtered and evaporated. The residue was purified by column chromatography using hexane:ethyl acetate 6:4 (v/v) to give 50 (40.0 mg, 35%).

R$_F$=0.35 hexane:ethyl acetate 1:1 (v/v); $^1$H NMR δ 5.28-5.21 (m, 2H, H-3, H-4), 4.79, 4.63 (2m, 2H, Cl$_3$CCH$_2$), 4.56 (d, 1H, H-1, J$_{1,2}$=8.2 Hz), 4.25, 4.14 (2m, 2H, H-6, H-6'), 3.82 (m, 1H, H-2), 3.70-3.55 (m, 4H, H-5, αCH, CH$_2$), 2.16, 2.08, 2.02 (3s, 9H, 3Ac), 1.44 (s, 9H, 3×Boc CH$_3$), 1.28-1.23 (m, 18H, 9CH$_2$), 0.87 (t, 3H, CH$_3$); FAB MS C$_{32}$H$_{53}$Cl$_3$N$_2$O$_{12}$ (764.13) m/z (%) 787 [M+Na]$^+$ (100), 462 [M−lipid]$^+$ (75), 663 [M−Boc+H]$^+$ (70).

tert-Butyl 1-[(2-acetamido-3,4,6-tri-O-acetyl-2-deoxy-β-D-glucopyranosyloxy)-methyl]-(R/S)-undecylcarbamate (51)

tert-Butyl 1-{[3,4,6-tri-O-acetyl-2-deoxy-2-(2,2,2-trichloro-ethoxycarbonyl-amino)-β-D-glucopyranosyloxy]methyl}-(R/S)-undecyl-carbamate 50(27.0 mg, 0.0353 mmol) was dissolved in acetic anhydride (1 ml) into which activated zinc powder (4.6 mg, 0.0706 mmol) had been added. The reaction was stirred for 6 hours, after which it was filtered and evaporated (and co-evaporated with benzene and toluene). The residue was purified by column chromatography to give 51 (11 mg, 49%).

$R_F$=0.17 hexane:ethyl acetate 1:1 (v/v); $^1$H NMR δ 5.24-5.16 (m, 2H, H-3, H-4), 4.51 (d, 1H, H-1, $J_{1,2}$=8.5 Hz), 4.27, 4.11 (2m, 2H, H-6, H-6'), 3.72 (m, 1H, H-2), 3.71-3.57 (m, 4H, H-5, αCH, CH$_2$), 2.16, 2.08, 2.02, 1.96 (4s, 12H, 4Ac), 1.43 (s, 9H, 3×Boc CH$_3$), 1.29-1.24 (m, 18H, 9CH$_2$), 0.87 (t, 3H, CH$_3$); FAB MS C$_{31}$H$_{54}$N$_2$O$_{11}$ (630.77) m/z (%) 653 [M+Na]$^+$ (60), 531 [M−Boc+H]$^+$ (90).

Example 12

Preparation of Glycosyl Isothiocyanates 2,3,4,6-tetra-O-acetyl-β-D-glucopyranosyl isothiocyanate (52)

Potassium thiocyanate (2.81 g, 28.7 mmol), tetrabutylammonium hydrogen sulphate (1.22 g, 3.59 mmol) and molecular sieves (6.00 g) were stirred in absolute acetonitrile (500 ml) for 30 minutes. 2,3,4,6-tetra-O-acetyl-α-D-glucopyranosyl bromide 37 (5.90 g, 14.4 mmol) was then dissolved in acetonitrile, added to the reaction flask and refluxed for 90 minutes. The solution was then allowed to cool, filtered through a celite pad and concentrated. Purification by column chromatography in hexane:ethyl acetate 2:1 (v/v) to give 52 (4.26 g, 76%).

$R_F$=0.29 hexane:ethyl acetate 3:2 (v/v); $^1$H NMR δ 5.20 (t, 1H, H-2), 5.09 (m, 2H, H-3, H-4), 5.02 (d, 1H, H-1, $J_{1,2}$=8.7 Hz), 4.24, 4.14 (2m, 2H, H-6, H-6'), 3.74 (m, 1H, H-5), 2.09, 2.01, 2.00 (3s, 12H, 4Ac); $^{13}$C NMR δ 170.6, 170.1, 169.1, 168.9, 144.3, 83.5, 74.1, 72.5, 71.9, 61.8, 61.5, 20.6, 20.5, 20.5, 20.4; FAB MS C$_{15}$H$_{19}$NO$_9$S (389.38) m/z (%) 412 [M+Na]$^+$ (8), 522 [M+Cs]$^+$ (25), 331 [M−NCS]$^+$ (100).

Cognate preparation of 2,3,4,6-tetra-O-acetyl-β-D-galactopyranosyl isothiocyanate (53)

$R_F$=0.38 hexane:ethyl acetate 3:2 (v/v); yield 79%; $^1$H NMR δ 5.39 (d, 1H, H-4), 5.28 (m, 1H, H-2), 4.99 (dd, 1H, H-3), 4.96 (m, 1H, H-1, $J_{1,2}$=8.9 Hz), 4.12 (m, 2H, H-6, H-6'), 3.95 (m, 1H, H-5), 2.16, 2.10, 2.04, 1.98 (4s, 12H, 4Ac); FAB MS C$_{15}$H$_{19}$NO$_9$S (389.38) m/z (%) 412 [M+Na]$^+$ (5), 522 [M+Cs]$^+$ (50), 331 [M−NCS]$^+$ (100).

Cognate preparation of 2,3,4,6-tetra-O-acetyl-α-D-mannopyranosyl isothiocyanate (54)

$R_F$=0.40 hexane:ethyl acetate 1:1 (v/v); yield 84%; $^1$H NMR δ 5.55 (d, 1H, H-1, $J_{1,2}$=2.0 Hz), 5.32 (m, 1H, H-2), 5.27 (m, 2H, H-3, H-4), 4.27, 4.14 (2m, 2H, H-6, H-6'), 4.08 (m, 1H, H-5), 2.17, 2.10, 2.06, 2.01 (4s, 12H, 4Ac); $^{13}$C NMR δ 170.7, 170.4, 169.9, 169.8, 144.1, 82.8, 71.6, 69.7, 68.3, 65.4, 61.6, 20.7, 20.6, 20.5, 14.2; FAB MS C$_{15}$H$_{19}$NO$_9$S (389.38) m/z (%) 412 [M+Na]$^+$ (5), 522 [M+Cs]$^+$ (70), 331 [M−NCS]$^+$ (100).

Cognate preparation of 2-acetamido-3,4,6-tri-O-acetyl-2-deoxy-β-D-glucopyranosyl isothiocyanate (55)

Purification by column chromatography in hexane:ethyl acetate 3:2 (v/v) to give 55 (1.09 g, 74%). $R_F$=0.38 hexane:ethyl acetate 3:1 (v/v); $^1$H NMR δ 5.94 (d, 1H, NH), 5.24 (t, 1H, H-3), 5.24 (d, 1H, H-1, $J_{1,2}$=9.6 Hz), 5.06 (t, 1H, H-4), 4.21, 4.11 (2m, 2H, H-6, H-6'), 3.99 (m, 1H, H-2), 3.75 (m, 1H, H-5), 2.09 (s, 3H, NAc), 2.04, 2.02, 2.00 (3s, 9H, 3OAc); $^{13}$C NMR δ δ 170.7, 170.6, 169.5, 169.2, 143.2, 83.9, 73.9, 71.8, 68.0, 61.7, 56.0, 23.2, 20.7, 20.6, 20.5; FAB MS C$_{15}$H$_{20}$N$_2$O$_8$S (388.39) m/z (%) 411 [M+Na]$^+$ (20), 521 [M+Cs]$^+$ (65), 330 [M−NCS]$^+$ (100).

Methyl 5-acetamido-3,5-dideoxy-β-D-glycero-D-galacto-2-nonulo-pyranosonate (56)

5-Acetamido-3,5-dideoxy-α/β-D-glycero-D-galacto-2-nonulo-pyranosonic acid (2.00 g, 6.46 mmol) was suspended in absolute methanol (60 ml) with ion exchange resin and stirred for 72 hours. The resin was subsequently filtered off and washed with methanol. The solution was concentrated and purified by column chromatography to give 56 (1.94 g, 93%).

$R_F$=0.60 chloroform:methanol:water 5:6:2 (v/v/v); $^1$H NMR δ 4.00-3.94 (m, 2H, H-4, H-6), 3.83 (t, 1H, H-5), 3.76 (s, 3H, OCH$_3$), 3.74 (dd, 1H, H-9'), 3.63 (dd, 1H, H-8), 3.53 (dd, 1H, H-9), 3.46 (d, 1H, H-7), 2.22 (dd, 1H, H-3$_{eq}$), 1.82 (dd, 1H, H-3$_{ax}$); FAB MS C$_{12}$H$_{21}$NO$_9$ (323.29) m/z (%) 324 [M+H]$^+$ (5), 346 [M+Na]$^+$ (100).

Methyl 5-acetamido-2,4,7,8,9-penta-O-acetyl-3,5-dideoxy-α/β-D-glycero-D-galacto-2-nonulo-pyranosonate (57)

Methyl 5-acetamido-3,5-dideoxy-β-D-glycero-D-galacto-2-nonulo-pyranosonate 56 (1.94 g, 6.01 mmol) was dissolved in pyridine (22.6 ml) and acetic anhydride (25.6 ml) and stirred overnight. The pyridine was evaporated and the residue co-evaporated with toluene and benzene. Purification by column chromatography gave 57α (570 mg, 18%) and 57β (1.58 g, 49%).

57α:

$R_F$=0.40 ethyl acetate:methanol 10:0.5 (v/v); $^1$H NMR δ 5.36 (dd, 2H, NH, H-7), 5.19 (dd, 1H, H-8), 5.04-4.99 (m, 1H, H-4), 4.68 (dd, 1H, H-6), 4.36 (dd, 1H, H-9'), 4.16 (m, 1H, H-5), 4.06 (dd, 1H, H-9), 3.76 (s, 3H, OCH$_3$), 2.56 (dd, 1H, H-3$_{eq}$), 2.07 (dd, 1H, H-3$_{ax}$), 2.12, 2.09, 2.02, 1.89 (4s, 18H, 6Ac); FAB MS C$_{22}$H$_{31}$NO$_{14}$ (533.48) m/z (%) 534 [M+H]$^+$ (5), 556 [M+Na]$^+$ (37), 414 (100).

57β:

$R_F$=0.30 ethyl acetate:methanol 10:0.5 (v/v); $^1$H NMR δ 5.37 (dd, 1H, H-7), 5.31-5.22 (m, 2H, H-4, NH), 5.06 (dd, 1H, H-8), 4.49 (dd, 1H, H-9'), 4.15-4.07 (m, 3H, H-5, H-6, H-9), 3.76 (s, 3H, OCH$_3$), 2.55 (dd, 1H, H-3$_{eq}$), 2.14 (dd, 1H, H-3$_{ax}$), 2.16, 2.08, 2.04, 1.89 (4s, 18H, 6Ac); FAB MS C$_{22}$H$_{31}$NO$_{14}$ (533.48) m/z (%) 534 [M+H]$^+$ (2), 556 [M+Na]$^+$ (38), 414 (100).

Methyl 5-acetamido-4,7,8,9-tetra-O-acetyl-2-chloro-3,5-dideoxy-β-D-glycero-D-galacto-2-nonulo-pyranosonate (58)

HCl gas was bubbled through acetyl chloride (150 ml) for 15 minutes at −15° C. to form a saturated solution. Methyl 5-acetamido-2,4,7,8,9-penta-O-acetyl-3,5-dideoxy-α/β-D-glycero-D-galacto-2-nonulo-pyranosonate 57 (700 mg, 1.31 mmol) was added to the solution, which was stirred for 24 hours. The acetyl chloride was evaporated and the residue co-evaporated with toluene and benzene. Purification by column chromatography using ethyl acetate gave 58 (582 mg, 87%).

$R_F$=0.5 ethyl acetate:methanol 10:0.5 (v/v); $^1$H NMR δ 5.51 (d, 1H, NH), 5.47 (dd, 1H, H-7), 5.38 (m, 1H, H-4), 5.16 (m, 1H, H-8), 4.43 (dd, 1H, H-9'), 4.36 (dd, 1H, H-6), 4.21 (m, 1H, H-5), 4.08 (m, 1H, H-9), 3.87 (s, 3H, OCH$_3$), 2.76 (dd, 1H, H-3$_{eq}$) 2.27 (dd, 1H, H-3$_{ax}$), 2.12, 2.09, 2.05, 1.90 (4s, 15H, 5Ac); FAB MS C$_{20}$H$_{28}$ClNO$_{12}$ (509.89) m/z (%) 532 [M+Na]$^+$ (47), 496 (100).

Methyl 5-acetamido-4,7,8,9-tetra-O-acetyl-2-isothiocyanato-3,5-dideoxy-α-D-glycero-D-galacto-2-nonulopyranosonate (59)

Potassium thiocyanate (1.10 g, 11.3 mmol), tetrabutylammonium hydrogen sulphate (478 mg, 1.41 mmol) and molecular sieves (3.00 g) were stirred in absolute acetonitrile (300 ml) for 30 minutes. Methyl 5-acetamido-4,7,8,9-tetra-O-acetyl-2-chloro-3,5-dideoxy-β-D-glycero-D-galacto-2-nonulopyranosonate 58 (2.86 g, 5.63 mmol) was then dissolved in acetonitrile, added to the reaction flask and refluxed for 1 hour. The solution was then allowed to cool, filtered through a celite pad and concentrated. Purification by column chromatography gave 59 (2.01 g, 67%).

$R_F$=0.21 chloroform:methanol 10:1 (v/v); $^1$H NMR δ 6.45 (d, 1H, NH), 5.42 (dd, 1H, H-7, $J_{7,8}$=7.3 Hz), 5.22 (m, 1H), 5.17 (m, 1H), 4.37 (dd, 1H), 4.16 (m, 2H), 4.05 (m, 1H), 3.89 (s, 3H, COOCH$_3$), 2.48 (dd, 1H, H-3$_{eq}$), 2.23 (dd, 1H, H-3$_{ax}$), 2.10, 2.06, 2.03, 1.89 (4s, 15H, 5Ac); $^{13}$C NMR δ 170.8, 170.5, 170.3, 170.0, 169.9, 169.7, 145.4, 107.9, 89.5, 76.8, 76.5, 73.5, 70.6, 69.7, 68.8, 68.5, 67.9, 67.8, 67.5, 67.0, 62.1, 61.9, 59.1, 53.9, 49.2, 48.9, 46.8, 38.9, 38.3, 24.2, 23.1, 20.9, 20.7, 19.6, 13.9; FAB MS C$_{21}$H$_{28}$N$_2$O$_{12}$S (532.52) m/z (%) 533 [M+H]$^+$ (20), 555 [M+Na]$^+$ (60), 571 [M+K]$^+$ (100), 665 [M+Cs]$^+$ (70).

Example 13

Reaction of Glycosyl Isothiocyanates with Alcohols to Form Thiocarbamate Linkages

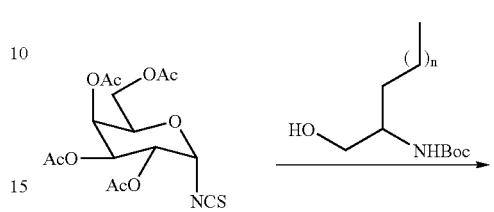

Example 15

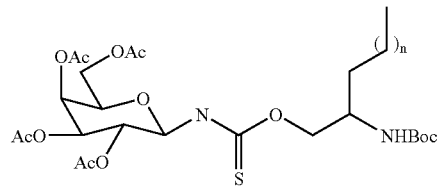

2,3,4,6-tetra-O-acetyl-N-[({2-(R/S)-[(tert-butoxycarbonyl)amino]-dodecyl}oxy)-carbonothioyl]-β-D-glucopyranosylamine (60)

2,3,4,6-tetra-O-cetyl-β-D-glucopyranosyl isothiocyanate 52 (1.00 g, 2.57 mmol), tert-butyl N-[1-(R/S)-(hydroxymethyl)undecyl]-carbamate 46 (967 mg, 3.21 mmol) and triethylamine (130 mg, 1.29 mmol) were dissolved in abs. toluene (10 ml) and stirred under reflux for 12 hours. Following evaporation, the residue was purified by column chromatography in hexane:ethyl acetate 2:1 to give 60 (1.36 g, 77%).

$R_F$=0.69 chloroform:methanol 10:2 (v/v); $^1$H NMR δ 67.02 (d, 1H, NH), 5.54, 5.32, 5.05, 4.96 (4m, 4H, H-1, H-2, H-3, H-4), 4.37 (m, 1H, αCH), 4.28 (m, 1H, H-6), 4.09 (m, 3H, CH$_2$, H-6'), 3.81 (d, 1H, H-5), 2.05, 2.01, 2.00, 1.99 (4s, 12H, 4Ac), 1.41 (s, 9H, 3×Boc CH$_3$), 1.28-1.21 (m, 18H, 9CH$_2$), 0.85 (t, 3H, CH$_3$); $^{13}$C NMR δ 170.6, 170.4, 169.9, 169.4, 155.3, 83.2, 81.9, 73.7, 72.7, 70.5, 69.8, 68.3, 67.6, 65.8, 61.6, 61.2, 60.2, 52.9, 49.6, 31.8-13.9; FAB MS C$_{34}$H$_{54}$N$_2$O$_{12}$S (690.84) m/z (%) 713 [M+Na]$^+$ (25), 823 [M+Cs]$^+$ (100), 591 [M−Boc+H]$^+$. (40).

Cognate preparation of 2,3,4,6-tetra-O-acetyl-N-[({2-(R/S)-[(tert-butoxycarbonyl)amino] tetradecyl}oxy)-carbonothioyl]-β-D-gluco-pyranosylamine (61)

$R_F$=0.29 chloroform:methanol 10:0.2 (v/v); yield 72%; $^1$H NMR δ 7.05 (d, 1H, NH), 5.53-4.99 (2m, 4H, H-1, H-2, H-3, H-4), 4.34 (m, 1H, αCH), 4.28-4.06 (m, 4H, H-6, H-6', CH$_2$,), 3.79 (d, 1H, H-5), 2.07, 2.03, 2.02, 1.99 (4s, 12H, 4Ac), 1.43 (s, 9H, 3×Boc CH$_3$), 1.25 (m, 22H, 11CH$_2$), 0.87 (t, 3H, CH$_3$); FAB MS C$_{36}$H$_{58}$N$_2$O$_{12}$S (718.90) m/z (%) 719 [M+H]$^+$ (10), 851 [M+Cs]$^+$ (50), 619 [M−Boc+H]$^+$ (70).

Example 14

Preparation of Aminomethyl Lipidic Amines tert-Butyl N-[1-(R/S)-(iodomethyl)undecyl]carbamate (62)

Trimethylphosphine (1.0M, 1.33 mmol) was added dropwise to a stirred solution of (azodicarbonyl)dipiperidine [ADDP] (336 mg, 1.33 mmol) in abs. THF (25 ml) at 0° C. After 30 minutes, iodomethane (189 mg, 1.33 mmol) and tert-butyl N-[1-(R/S)-(hydroxy-methyl)undecyl]carbamate 46 (200 mg, 0.664 mmol) were added to the solution, which was subsequently stirred for 4 hours at room temperature. The precipitate was then filtered off and the solution evaporated to dryness. The residue was dissolved in ethyl acetate and the remaining hydrazide was precipitated from hexane and removed by filtration. Following evaporation, the residue was taken up in $CH_2Cl_2$ (50 ml), washed with water (2×25 ml) and with $NaHCO_{3\,(sat,\,aq)}$ (1×25 ml), dried with $MgSO_4$, filtered and evaporated. The residue was purified by column chromatography in hexane:ethyl acetate 4:1 (v/v) to give 62 (176 mg, 64%).

$R_F$=0.79 hexane:ethyl acetate 1:1 (v/v); $^1$H NMR δ 4.47 (d, 1H, NH), 3.24 (m, 1H, αCH), 2.15, 1.84 (2d, 2H, $CH_2I$), 1.40 (s, 9H, 3×Boc $CH_3$), 1.23 (m, 18H, $9CH_2$), 0.83 (t, 3H, $CH_3$); $^{13}$C NMR δ 155.1, 80.8, 49.6, 38.2-22.6, 15.1, 14.0; FAB MS $C_{17}H_{34}INO_2$ (411.36) m/z (%) 410 [M−H]$^+$ (100), 434 [M+Na]$^+$ (30), 544 [M+Cs]$^+$ (85), 340 [M−Boc+H]$^+$ (100).

tert-Butyl N-[1-(R/S)-(azidomethyl)undecyl]carbamate (63)

tert-Butyl N-[1-(R/S)-(iodomethyl)undecyl]carbamate 62 (250 mg, 0.608 mmol) was dissolved in abs. DMF (10 ml). Sodium azide (79.0 mg, 1.22 mmol) was added to the solution, which was subsequently stirred at 110° C. for 12 hours. Following evaporation, the residue was taken up in $CH_2Cl_2$ (50 ml) and was washed with $NaHCO_{3(sat,\,aq)}$ (1×50 ml). The organic phase was dried over $MgSO_4$, filtered and evaporated. The residue was purified by column chromatography in hexane:ether 10:1 (v/v) to give 63 (100 mg, 54%).

$R_F$=0.46 hexane:ethyl acetate 5:1 (v/v); $^1$H NMR δ 3.61 (m, 1H, αCH), 3.46-3.39 (m, 2H, $CH_2$), 1.43 (s, 9H, 3×Boc $CH_3$), 1.25 (m, 18H, $9CH_2$), 0.87 (t, 3H, $CH_3$); ESI MS $C_{17}H_{34}N_4O_2$ (326.48) m/z (%) 327 [M+H]$^+$ (100), 349 [M+Na]$^+$ (15), 227 [M−Boc+H]$^+$ (20).

tert-Butyl N-[1-(R/S)-(aminomethyl)undecyl]carbamate (64)

Palladium catalyst (10% on carbon, 10.0 mg) was added in one portion to a solution of tert-butyl N-[1-(azidomethyl)undecyl]-carbamate 63 (100 mg, 0.282 mmol) in abs. methanol (5 ml) under a hydrogen atmosphere. The solution was allowed to stir for 12 hours. The catalyst was subsequently filtered off, and the solvent evaporated to give 64 (78 mg, 84%).

$R_F$=0.59 hexane:ethyl acetate 1:1 (v/v); $^1$H NMR δ 4.92 (d, 1H, NH), 3.74 (m, 1H, αCH), 3.05 (m, 2H, $CH_2$), 1.45 (s, 9H, 3×Boc $CH_3$), 1.25 (m, 18H, $9CH_2$), 0.88 (t, 3H, $CH_3$);

FAB MS $C_{17}H_{36}N_2O_2$ (300.48) m/z (%) 301 [M+H]$^+$ (55), 323 [M+Na]$^+$ (20), 201 [M−Boc+H]$^+$ (85).

Example 15

Reaction of Glycosyl Isothiocyanates with Amines to Form Thiourea Linkages

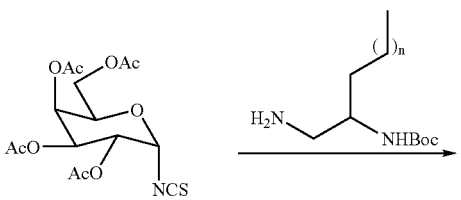

Example 17

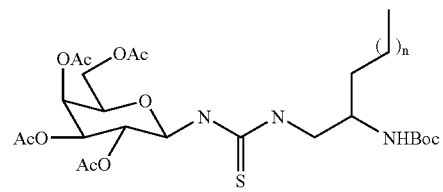

2,3,4,6-tetra-O-acetyl-N-[({2-(R/S)-[(tert-butoxycarbonyl)amino]-dodecyl}amino)-carbonothioyl]-β-D-glucopyranosylamine (65)

2,3,4,6-tetra-O-acetyl-β-D-glucopyranosyl isothiocyanate 37 (25.0 mg, 0.0617 mmol), tert-butyl N-[1-(R/S)-(aminomethyl)-undecyl]carbamate (27.8 mg, 0.0927 mmol) and triethylamine (12.5 mg, 0.0124 mmol) were dissolved in abs. $CH_2Cl_2$ (5 ml) and stirred at room temperature for 1 hour. Following evaporation, the residue was purified by column chromatography to give 65 (42.0 mg, 94%)

$R_F$=0.39 chloroform:methanol 10:0.2 (v/v); $^1$H NMR δ 5.11-4.99 (m, 3H, H-1, H-3, H-4), 4.23, 4.10 (2m, 2H, H-6, H-6'), 3.87-3.61 (m, 3H, H-2, H-5, αCH), 2.09, 2.01, 2.00, 1.96 (4s, 12H, 4Ac), 1.43 (s, 9H, 3×Boc $CH_3$), 1.24 (m, 18H, $9CH_2$), 0.88 (t, 3H, $CH_3$); FAB MS $C_{32}H_{55}N_3O_{11}S$ (689.86) m/z (%) 690 [M+H]$^+$ (10), 712 [M+Na]$^+$ (30), 590 [M−Boc+H]$^+$ (100).

Cognate preparation of 2,3,4,6-tetra-O-acetyl-N-[({2-(R/S)-[(tert-butoxycarbonyl)amino]tetradecyl}-amino)carbonothioyl]-β-D-gluco-pyranosylamine (66)

Procedure as for 65 $R_F$=0.41 chloroform:methanol 10:0.2 (v/v); yield 85%; $^1$H NMR δ 5.16-4.96 (m, 3H), 4.28, 4.11 (2m, 2H, H-6, H-6'), 3.84-3.58 (m, 3H, H-2, H-5, αCH), 2.11, 2.06, 2.04, 2.00 (4s, 12H, 4Ac), 1.44 (s, 9H, 3×Boc $CH_3$), 1.25 (m, 22H, $11CH_2$), 0.84 (t, 3H, $CH_3$); FAB MS $C_{34}H_{59}N_3O_{11}S$ (717.91) m/z (%) 718 [M+H]$^+$ (40), 618 [M−Boc+H]$^+$ (85).

Example 16

Multiple Charged Lipid-Sugar Delivery Systems

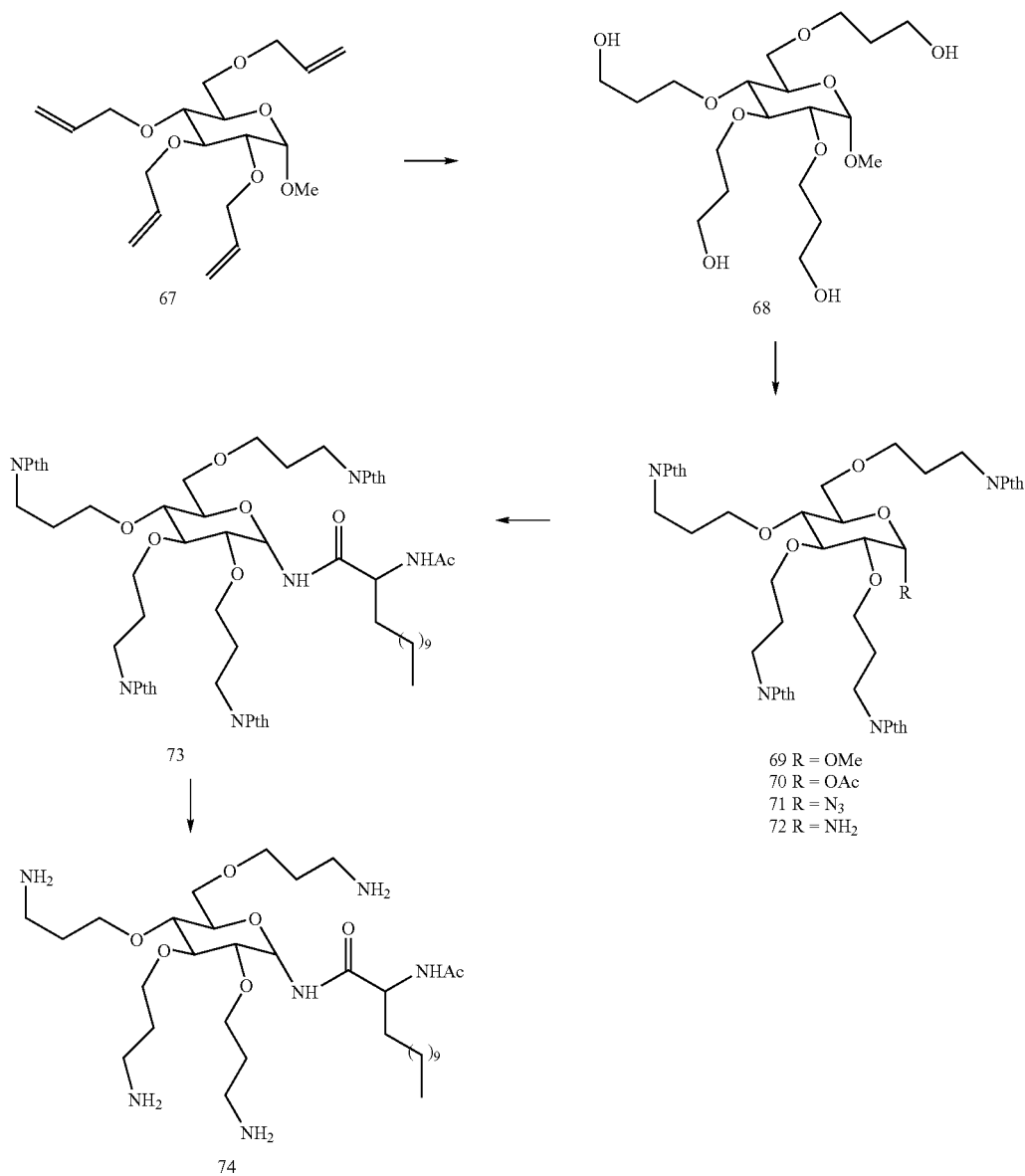

Compound 67 is readily prepared from commercially—available starting materials by known literature methods.

Methyl 2,3,4,6-tetra-O-(3-hydroxypropyl)-α-D-glucopyranoside (68).

To a solution of 67 (1.03 g, 2.9 mmol) in dry THF (25 mL) 9-BBN (0.5M solution in THF; 70 mL, 35 mmol) was added under nitrogen and the reaction was stirred at reflux for 6 h. Then the excess of 9-BBN was destroyed by dropwise addition of water (3.0 mL) at 0° C. The hydroboration mixture was oxidized by adding 3M aq Na acetate (36 mL) and 30% $H_2O_2$ (36 mL) slowly at 0° C. followed by stirring overnight at room temperature. The aqueous phase was saturated with $K_2CO_3$ and the THF phase was separated. The aqueous phase was extracted with THF (2×50 mL). The combined THF layers were dried over $MgSO_4$, filtered, and concentrated. The oily residue was purified by column chromatography (9:1→8:2 $CHCl_3$-MeOH) to yield a colorless oil (0.86 g, 70%).

$R_f$ 0.26 $CHCl_3$-MeOH; 8:2): FAB MS 449 (M+Na)$^+$, 427 (M+H)$^+$; $^1$H NMR (500 MHz, $CDCl_3$): δ 1.77-1.82 (m, 8H, 4 $OCH_2CH_2CH_2OH$), 3.24 (dd, 1H, $J_{4,5}$ 9.2 Hz, H-4), 3.28 (dd, 1H, H-2), 3.38 (s, 3H, $OCH_3$), 3.48 (1H, t, $J_{3,4}$ 9.5 Hz, H-3), 3.52-3.74 (m, 16H, 4 $OCH_2CH_2CH_2OH$), 3.80 (m, 1H, H-6), 3.82-3.87 (m, 2H, H-5, H-6'), 4.80 (1H, d, $J_{1,2}$ 3.5 Hz, H-1).

Anal. Calcd for $C_{19}H_{38}O_{10}$: C, 53.51; H, 9.00. Found: C, 53.60; H, 8.72

Methyl 2,3,4,6-tetra-O-3-phthalimidopropyl-α-D-glucopyranoside (69).

To a solution of 68 (0.48 g, 1.13 mmol), phthalimide (0.93 g, 6.30 mmol), and triphenylphosphine (1.57 g, 6.0 mmol) in dry THF (40 mL) diethyl azodicarboxylate (DEAD) (0.93 mL, 5.9 mmol) dissolved in dry THF (5 mL) was added dropwise and the reaction was stirred at room temperature under $N_2$ for 72 h. The solvent was evaporated in vacuo and the residue dissolved in $CH_2Cl_2$ (50 mL) was washed with brine and dried ($MgSO_4$), filtered and concentrated in vacuo. Purification of the residue with ethyl acetate-hexane (8:2) eluent afforded the product (1.0 g, 94%).

$R_f$ 0.28 EtOAc-hexane; 7:3); $[\alpha]^{24}D$ +28.5 (c 1.0, $CHCl_3$); FAB MS: 966 (M+Na)$^+$, 943 (M)$^+$; $^1$H NMR(500 MHz, $CDCl_3$): δ 1.91-1.98 (m, 8H, 4 $OCH_2CH_2CH_2NPht$), 3.06-3.11 (m, 2H, H-4, H-2), 3.29 (s, 3H, $OCH_3$), 3.43 (t, 1H, $J_{3,4}$ 9.5 Hz, H-3), 3.46-3.63 (m, 8H, 4 $OCH_2CH_2CH_2NPht$), 3.65-3.92 (m, 11H, 4 $OCH_2CH_2CH_2NPht$, H-5, H-6, H-6'), 4.70 (d, 1H, $J_{1,2}$ 3.5 Hz, H-1), 7.45-7.80 (16H, m, 4 ArH); $^{13}$C NMR (62.9 Hz, $CDCl_3$): 28.8, 29.3, 29.4, 29.6 ($OCH_2CH_2CH_2NPht$), 35.3, 35.7, 35.8 ($OCH_2CH_2CH_2NPht$), 54.9 ($OCH_3$), 68.7, 69.2, 69.8, 70.0, 70.6, 71.0, 76.5 ($OCH_2CH_2CH_2NPht$, C-5, C-6), 78.24 (C-4), 80.8 (C-2), 81.9 (C-3), 97.7 (C-1), 123.0, 123.1, 131.9, 132.0, 132.2, 132.4, 133.7, 133.8 (ArC), 168.2 (CONPht);

Anal. Calcd for $C_{51}H_{50}O_{14}N_4$: C, 64.96; H, 5.34. Found: C, 64.68; H, 5.42.

1-O-Acetyl-2,3,4,6-tetra-O-3-phthalimidopropyl-α-D-glucopyranose (70).

A solution of 69 (1.0 g, 1.06 mmol) in acetic anhydride (10 mL) was stirred at −20° C. for 10 min. To this stirred solution was added precooled (0° C.) $Ac_2O/H_2SO_4$ (50:1, 5 mL) in 5 min, and the reaction mixture was left at −20° C. for 3 days. The reaction mixture was diluted with dichloromethane (100 mL) and was washed successively with sat. $NaHCO_3$ (50 mL) and water (50 mL). The organic layer was dried ($MgSO_4$), filtered, and concentrated in vacuo and co-distilled with toluene several times. The residue was purified on silca gel column with ethyl acetate-hexane (7:3) solvent to yield a colorless oil (0.8 g, 78%).

$R_f$ 0.19); FAB MS 1104 (M+Cs)$^+$, 994 (M+Na)$^+$; $^1$H NMR(500 MHz, $CDCl_3$): δ 1.91-1.95 (m, 8H, 4 $OCH_2CH_2CH_2NPht$), 2.10 (s, 3H, OAc), 3.14-3.19 (2H, m, H-4, H-2), 3.40 (m, 1H, H-3), 3.45 (m, 1H, H-6), 3.51-3.79 (m, 17H, H-6', 4 $OCH_2CH_2CH_2NPht$, 3.82-3.90 (m, 2H, H-3, H-5), 6.12 (1H, d, $J_{1,2}$ 3.5 Hz, H-1), 7.45-7.80 (m, 16H, 4ArH); $^{13}$C NMR (62.9 Hz, $CDCl_3$): δ 21.0 (Ac—C-1) 28.8, 29.2, 29.4, 29.5 ($OCH_2CH_2CH_2NPht$), 35.3, 35.6 ($OCH_2CH_2CH_2NPht$), 68.5, 69.3, 69.3, 70.9, 71.1, 72.8, 76.5 ($OCH_2CH_2CH_2NPht$, C-5, C-6), 77.5 (C-4), 79.7 (C-2), 81.6 (C-3), 89.6 (C-1), 123.0, 123.1, 131.9, 132.0, 132.2, 132.3, 133.7, 133.7 (ArC), 168.2 (CONPht).

Anal. Calcd for $C_{52}H_{50}O_{15}N_4$: C, 64.32; H, 5.19. Found: C, 64.41; H, 5.22.

2,3,4,6-Tetra-O-3-phthalimidopropyl-α/β-D-glucopyranosyl azide (71).

A solution of 70 (0.44 g, 0.45 mmol) in dry $CH_2Cl_2$ (20 mL) was stirred with azidotrimethylsilane (0.15 mL, 1.13 mmol) and tin(IV)chloride (0.026 mL, 0.23 mmol) for 1 day. The solution was diluted with dichloromethane (20 mL) and washed with 1M KF solution (10 mL) then with water (10 mL). The organic extract was dried ($MgSO_4$), filtered, and concentrated to afford a white foam (0.36 g, 83%).

$R_f$ 0.30 EtOAc-hexane; 7:3); $[\alpha]^{24}D$ +51.8 (c 1.0, $CHCl_3$); FAB MS 977 (M+Na)$^+$, 955 (M+1)$^+$; $^1$H NMR(500 MHz, $CDCl_3$): 1.89-1.97 (m, 8H, 4 $OCH_2CH_2CH_2NPht$), 3.06-3.15 (m, 2H, H-2, H-4), 3.29 (t, 1H, $J_{2,3}$ 9.0 Hz, H-3), 3.44-3.87 (m, 19H, H-5, H-6, H-6', 4 $OCH_2CH_2CH_2NPht$), 5.36 (1H, d, $J_{1,2}$ 3.5 Hz, H-1), 7.45-7.80 (m, 16H, 4 ArH).

Anal. Calcd for $C_{50}H_{47}O_{13}N_7$: C, 63.47; H, 4.97. Found: C, 63.41; H, 4.88.

2,3,4,6-Tetra-O-3-phthalimidopropyl-α/β-D-glucopyranosylamine (72).

The azido sugar 71 (0.38 g, 0.4 mmol) dissolved in ethyl acetate (10 mL) was hydrogenated using Pd (10% on charcoal, 90 mg, 10%) catalyst for 2 days at room temperature. The catalyst was filtered off and washed with ethyl acetate (40 mL) and the filtrate was evaporated. The residue was purified with ethyl acetate-ether (9:1) eluent containing 0.5% triethylamine. The product (280 mg, 76%; $R_f$ 0.21) is a white foam.

FAB MS 951 (M+Na)$^+$, 928 (M)$^+$; $^1$H NMR(500 MHz, $CDCl_3$): δ 1.84-1.99 (m, 8H, 4 $OCH_2CH_2CH_2NPht$), 3.01-3.11 (m, 3H, H-4, H-2, H-3), 3.44-3.92 (m, 19H, H-5, H-6, H-6', 4 $OCH_2CH_2CH_2NPht$), 4.95 (t, 1H, H-1), 7.45-7.80 (m, 16H, 4 ArH); $^{13}$C NMR(62.9 Hz, $CDCl_3$): δ 28.7, 28.9, 29.4, 29.6 ($OCH_2CH_2CH_2NPht$), 35.4, 35.7 ($OCH_2CH_2CH_2NPht$), 69.3, 70.0, 70.2, 70.4, 70.8, 71.0, 75.6 ($OCH_2CH_2CH_2NPht$, C-5, C-6), 78.6 (C-4), 84.1 (C-2), 85.9 (C-3), 89.3 (C-1), 123.1, 131.88, 132.4, 133.5, 133.6, 133.7 (ArC), 166.2 (CONPht).

Anal. Calcd for $C_{50}H_{49}O_{13}N_5$: C, 64.72; H, 5.32. Found: C, 64.41; H, 5.12.

2,3,4,6-tetra-O-3-phthalimidopropyl-N-{1-(R/S)-[acetylamino]-dodecyl}-α/β-D-glucopyranosylamide (73).

The amino sugar 72 (140 mg, 0.15 mmol) was coupled with tbutoxycarbonylaminododecanoic acid according to the procedures in example 3 above to yield the Boc protected lipoaminoacid-sugar conjugate. This material was treated according to the methods described in example 6 to provide the corresponding free amino compound. Acetylation with acetic anhydride (17 mg, 1.7 mmol) in dry $CH_2Cl_2$ (5 mL) overnight in the presence of triethylamine (2 eq) followed by removal of the solvents in vacuo and column chromatography with $CHCl_3$-MeOH (93:7) yielded the desired product (130 mg, 84%).

2,3,4,6-tetra-O-3-aminopropyl-N-{1-(R/S)-[acetylamino]dodecyl}-α/β-D-glucopyranosylamide (74).

Compound 73 above is treated with ethylenediamine in dichloroethane at reflux for 18 hours. After this time, the solvents are removed in vacuo and the product dissolved in acetonitrile/water/acetic acid. The crude product mixture is separated by ion exchange chromatography and the fractions lyophilised to dryness. The resultant compound is a lipoaminoacid-sugar conjugate bearing 4 amino functions.

Example 17

Enhancing Oral Bioavailability of Gentamycin Sulfate In Vivo

A liposaccharide absorption enhancer, $C_{1-4}$ carboxylic acid (C14 AE) (1a), was used to enhance the oral bioavailability of gentamycin sulfate (GS) (2) in vivo.

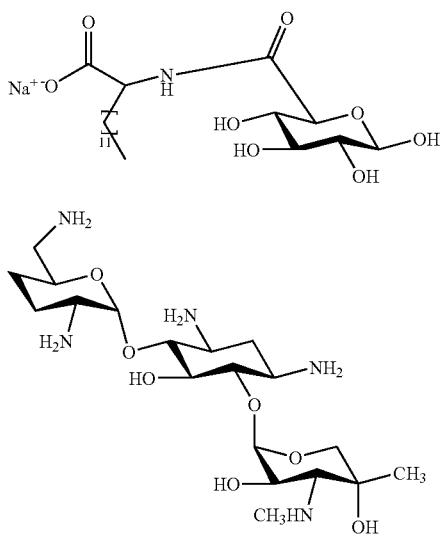

Gentamycin sulfate (GS) is an important antibiotic aminoglycoside extensively used in human and veterinary medicine. Exhibiting negligible oral bioavailability and rapid clearance, current formulations of GS demand peritoneal administration.

Method:

(i) Intra-Arterial Cannulation of the Femoral Artery

Male Sprague-Dawley rats (300-350 g) were anaesthetised with zoletil (60 mg/kg) and xylazine (12 mg/kg) given via the intraperitoneal route to facilitate insertion of a permanent polypropylene cannula into the femoral artery. Following surgery, the rats were allowed to recover overnight. A heparinised saline (50 IU in 5 mL) block was used in the cannula prevent the development of blood clots.

(ii) Pharmacokinetic Study

The following day after surgery, rats receiving the treatment were given the absorption enhancer C14 AE (100 mg/kg) combined with GS (60 mg/kg) dissolved together in 1 mL 0.5% DMSO/water, adjusted to pH 9. By comparison, control rats received gentamycin sulfate (60 mg/kg) only, dissolved in 1 mL of an identical 5% DMSO/water solvent. In all cases, the drug formulations were administered via oral gavage while under light anaesthesia with 50/50% $O_2:CO_2$. Following oral administration of the drug formulations, 0.5 ml blood samples were taken via the implanted intra-arterial cannula at regular pre-determined time points over a 6-hour experimental period (0, 15, 30, 45, 60, 90, 120, 240 and 360 mins post-dose). At the conclusion of the pharmacokinetic study, the rats were promptly euthanised.

Plasma was extracted from the whole blood samples following centrifugation (20,000 g, 4 min) and stored frozen at −70° C.

(iii) Plasma Assay

A plasma gentamycin assay currently in clinical use was performed. Plasma samples were assayed for gentamycin on an immunoassay analyser (Abbott AxSYM® System, Abbott Laboratories, IL) using a commercially available kit (Abbott AxSYM® Gentamycin assay, Abbott Laboratories, IL). The assay is based on Fluorescence Polarization Immunoassay (FPIA) technology as described in the literature (Jolley M E, Stroupe S D, Wang C J, et al. Fluorescence polarization immunoassay I. Monitoring aminoglycoside antibiotics in serum and plasma. *Clin. Chem.* 1981;27:1190-7). Assay calibration was performed with commercial AxSYM® Gentamycin Standard Calibrators (Abbott Laboratories, IL.) which contained accurately measured amounts of gentamycin prepared in human serum to yield the concentrations 0.0, 0.5, 1.5, 3.0, 6.0 and 10.0 μg/mL. The limit of detection of the assay was 0.30 μg/mL.

Results:

Pharmacokinetic Analysis

Mean GS concentrations in plasma as a function of time after oral administration of GS 60 mg/kg, either in conjunction with or without C14 AE 100 mg/kg are presented in FIG. 1. The mean pharmacokinetic parameter values derived from these plots are summarised in Table 1 below.

TABLE 1

Mean pharmacokinetic parameters obtained after single bolus oral administration of gentamycin sulfate (GS) 60 mg/kg either with or without the liposaccharide absorption enhancer, C14 carboxylic acid (C14 AE) 100 mg/kg

| Variables | Control (GS 60 mg/kg) | Treatment (GS 60 mg/kg + C14 AE 100 mg/kg) |
|---|---|---|
| AUC (ug min$^{-1}$ ml$^{-1}$) | 221.29 | 361.47 |
| $C_{max}$ (ug ml$^{-1}$) | 0.89 | 4.16 |
| $t_{max}$ (min) | 30 | 15 |

Discussion:

Co-administration of GS 60 mg/kg with C14 AE 100 mg/kg markedly increased the oral absorption of GS in comparison to the control administration of GS 60 mg/kg alone. Inspection of the plasma-concentration time curves (FIG. 1) indicates that when formulated with C14 AE, GS was rapidly absorbed from the stomach into the systemic circulation with $t_{max}$ occurring as early as 15 minutes post-dose. Most notably, mean $C_{max}$ in the treatment rats (4.16 μg ml$^{-1}$) was more than 4.5-fold higher than the equivalent value in controls (0.89 μg ml$^{-1}$) without causing obvious adverse reactions in the animal subjects. Although the peak concentrations observed in treatment rats are marginally below the therapeutic range of 5-10 μg ml$^{-1}$, it would not be inconceivable that the actual $C_{max}$ in treatment rats may be higher than that reported here with the real $t_{max}$ residing much earlier in the experimental time course.

There was no evidence of significant intestinal absorption of GS in either control or treatment rodents. While control rodents largely maintained earlier plasma concentrations of GS with only minor indications of intestinal absorption, the treatment rats presented no such biphasic mode of oral absorption with the curve literally tracing that for control rats at 120 minutes post-dose and beyond. This phenomenon is most likely due to masking effects following the elimination of stomach absorbed GS.

Overall, the GS plasma concentration profile produced following co-administration with C14 AE possesses characteristics more akin to single bolus parenteral drug administration than the oral route. This can be seen in the rapid rise in plasma GS concentrations post-dose with subsequent re-distribution into the various body compartments tissues. At 120 minutes post-dose however, a slow elimination curve is evident and occurs for both treatment and control rats. Additionally, C14 AE increased the AUC for GS by approximately 1.63-fold, a result largely due to the expanded degree of stomach absorption.

Conclusion:

The liposaccharide absorption enhancer, C14 AE, was highly efficient in increasing the oral absorption of gentamycin sulfate in conscious male Sprague-Dawley rats. In comparison to controls, the measured $C_{max}$ values for treatment rats was increased by more than 4.5-fold with potentially higher values actually occurring in the rodents during the interval between dose administration and the first sampling time point. While not wishing to be bound by theory, it is very likely that therapeutic levels of GS were absorbed via the oral route with a 1.63-fold increase in the AUC in treatment rats in comparison to controls.

In a similar manner, it is expected that other aminoglycoside antibiotics including neomycine, amikacin, tobramycin, and netilmicin could be delivered by the compositions of the present invention.

Example 18

Enhancing Oral Bioavailability of Low Molecular Weight Heparin In Vivo

Two liposaccharide absorption enhancers, C12 primary amine (3a) and C12 quaternary amine (4a), were investigated in improving the oral bioavailability of low molecular weight heparin (LMWH) (5a) (approx 3000 Mol Wt) in vivo.

This example was conducted in conscious male Sprague-Dawley rats (300-350 g) with all drug formulations administered via oral gavage. The three groups tested were as follows:
C12 primary amine/LMWH
C12 quaternary amine/LMWH, and
LMWH controls.

Method:

Initial attempts using the protocol described in Example 17 for the oral gentamycin delivery project proved to be unsuccessful due to major problems arising from the formation of significant blood clots in the intra-arterial cannula. Unlike most in vivo pharmacokinetic studies, it was not possible to use heparinised saline in the intra-arterial cannula to prevent blood clots due to its obvious potential to interfere with the assays for systemic heparin concentrations. Hence a saline infusion (0.5 ml/hr) was used to inhibit the occlusion of the cannula by blood clots.

(i) Pharmacokinetic Study

Following surgical recovery, rats receiving the experimental treatment were given either one of the absorption enhancers (200 mg/kg) combined with LMWH (Sigma, catalogue H 3400, 55 IU/mg) (2000 IU/kg) dissolved together in 5% DMSO/water. By comparison, control rats received LMWH (2000 IU/kg) only, dissolved in an identical solvent. In all cases, the drug formulation was administered via oral gavage whilst under light anaesthesia with 50/50% $O_2$:$CO_2$. Following oral administration of the drug formulations, 0.5 ml blood samples were obtained via the implanted intra-arterial cannula at regular pre-determined time points: 0, 0.25, 0.5, 1, 1.5, 2, 3, 4 and 6 hours post-dose. At the conclusion of the pharmacokinetic study, the rats were promptly euthanised.

Plasma was extracted from the whole blood samples following centrifugation (20 000 g, 4 min) and stored frozen at −70° C.

(ii) Plasma Assay

The plasma low molecular weight heparin (LMWH) assay was used to determine the concentrations of LMWH in the rat plasma. Plasma samples were assayed for LMWH using a commercially available anti-factor Xa kit (Berichrom® Heparin, Dade Behring Inc., Deerfield, Ill.) used in conjunction with a Sysmex® CA-6000 Coagulation Analyser. LMWH exerts an anticoagulant effect by catalysing the inactivation of factor Xa by antithrombin III (AT III). The use of anti-factor Xa activity as a marker for LMWH absorption is consistent with the literature (Arnold J, Ahsan F, Meezan E, Pillion D J. Nasal administration of low molecular weight heparin. J. Pharm. Sci. 2002;91(7):1707-14). In the assay, LMWH is analysed as a complex with AT III. Excess AT III is added to the plasma sample to obtain a constant AT III activity. Factor Xa, in excess, is inactivated by the [LMWH/AT III] complex. The residual factor Xa is measured amidolytically by a chromogenic peptide substrate in a kinetic test. The plasma LMWH concentration was determined by reference to a standard curve prepared from data obtained by analysis of normal rat plasma spiked with LMWH (same batch used to dose rats) to yield the concentrations 0.00, 0.06, 0.12, 0.25, 0.50, 1.00 IU/mL. The limit of detection of this assay was 0.07 IU/ml.

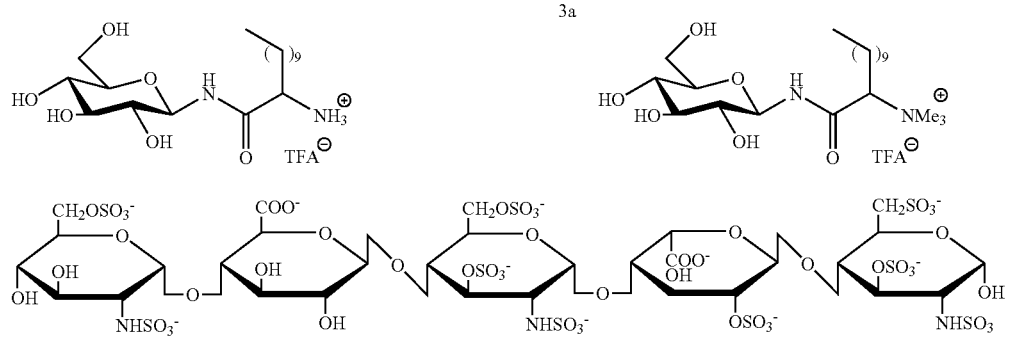

Considering that this assay was originally intended for human use, it was decided that validation of this assay for use with in rat plasma would be necessary. Hence, a number of blank rat plasma samples treated with known levels of heparin were assayed initially and a calibration curve constructed. In addition, quality control standards were used during the subsequent analysis of experimental samples to further confirm the accuracy of results. Altogether, the use of a human anti-factor Xa assay for rat plasma yielded accurate results and proved to be a suitable analytical option.

Figure 2:
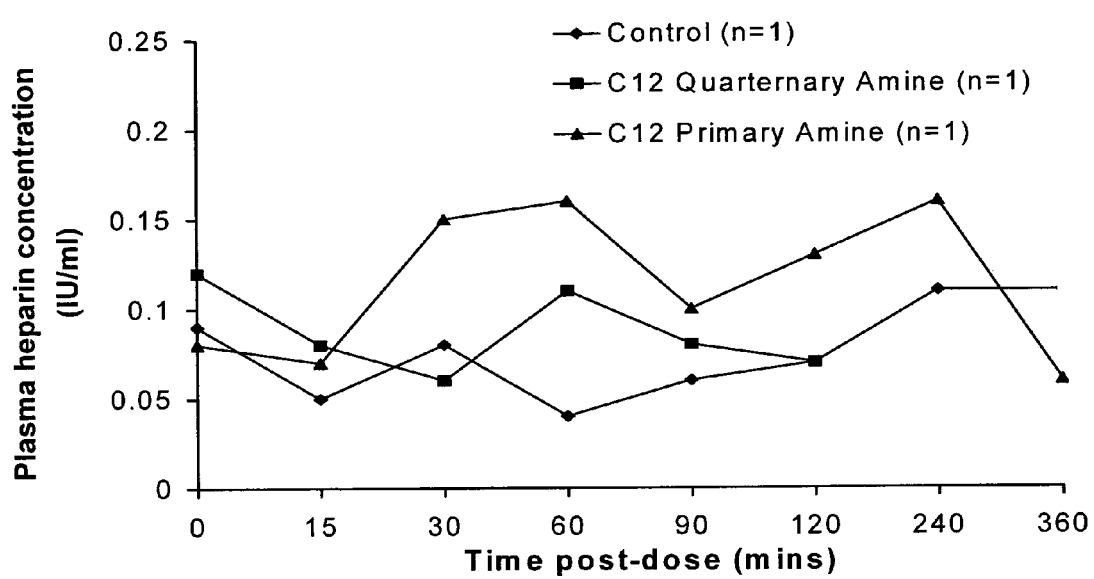
FIG. 2 is a graph showing the plasma heparin concentration in male Sprague-Dawley rats following administration of control, C12 Quaternary Amine and C12 Primary Amine as a function of time.

Results:

Using this method, a number of experiments investigating the two C12 absorption enhancers described were completed with the results summarised in FIG. 2.

As shown in FIG. 2, it appears that the C12 primary amine absorption enhancer in particular, increased the absorption of oral heparin in comparison to the control formulation. By contrast however, the C12 quaternary amine absorption enhancer only demonstrated modest efficacy. Inspection of the pharmacokinetic profile indicates two distinct phases for oral heparin absorption, specifically at approximately 60 and 240 minutes post-dose. These two peak absorption times reflect absorption initially in the stomach (60 mins) followed by later absorption in the intestine (240 mins) following gastric emptying of stomach contents into the intestinal tract.

In a similar manner it is expected that other heparinoid and sulphated or acidic oligosaccharides such as heparin, calciparine, enoxaparin, delteparin, nadroparin, danaparoid, fractionated low molecular weight heparin, fondoparaneux, PI-88, hyaluronic acids, chondroitin sulfates and physiologically acceptable salts thereof will be deliverable using the compositions of the present invention.

Calciparine is a trade name for the calcium salt of full length heparin; enoxaparin, delteparin, nadroparin, danaparoid are trade names for the sodium or calcium salts of fractionated low molecular weight heparin, and represent a range of oligomers typically from 4 to 25 saccharidic units.

It is further expected that fondoparaneux will demonstrate superior delivery over the results shown above, because fondoparaneux is a low molecular weight heparin analogue of discrete chemical composition.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention claimed is:

1. A compound of general Formula I, which is an ionic complex:

$r[D^{(nz)}]p[(W_q-S-X-L)^{(my)}]$        Formula I in which D is a therapeutically useful molecule selected from the group consisting of a drug, peptide, protein, nucleic acid, mono- or oligosaccharide, and sugar-peptide conjugate;

r is an integer greater than or equal to 1;

p, n and m may be the same or different, and are independently integers greater than or equal to 1;

n and m represent the overall magnitude of the charge on the molecules; and z and y are charges, either positive (+) or negative (−), such that when z is positive, y is negative and vice versa;

and is a carrier compound, in which

X is a covalent bond, or is a linker group, selected from 2 to 14 atom spacers, which may be optionally substituted, branched or linear;

S is a mono- or oligosaccharide;

L is a lipidic moiety;

W is a 3 to 10 atom alkyl or heteroalkyl spacer, which may be branched or linear, and is substituted with one or more functional groups, each of which is charged or is capable of carrying a charge under physiological conditions; and q is an integer, which ranges from 3 to the number of hydroxyls available for substitution on the mono- or oligosaccharide.

2. The compound of claim 1, in which D is a drug.

3. The compound of claim 1, in which the linker X is attached to the mono- or oligosaccharide S through the anomeric position.

4. The compound of claim 1, in which the linker X is attached to the mono- or oligosaccharide S via an 0-glycoside, C-glycoside, N-glycoside, S-glycoside, amide, urea, thiourea, carbamate, thiocarbamate, carbonate, ether or ester bond.

5. The compound of claim 1, in which the linker X is attached to the mono- or oligosaccharide S through a position other than the anomeric position via an amide, urea, thiourea, carbamate, thiocarbamate, carbonate, ether or ester bond.

6. The compound of claim 1, in which the linker X is attached to the lipidic moiety L via an amide, ester, ether, imine, carbamate, urea, thiourea, or carbonate linkage.

7. The compound of claim 1, in which W is substituted with one or more functional groups selected from the group consisting of an amidine, guanidinium, carboxylate, tetrazole, hydroxamic acid, hydrazide, amine, sulfate, phosphonate, phosphate and a sulfonate group.

8. The compound of claim 1, in which the lipidic moiety L is composed of:

(a) any combination of 1 to 4 lipoamino acids and/or lipoamino alcohols, of general Formula IIa or IIb

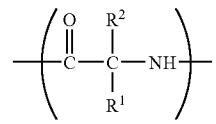

IIa

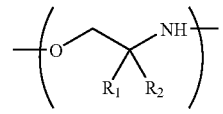

IIb in which each of $R^1$ and R2 may independently be:

(i) hydrogen, or (ii) a linear or branched chain alkyl or alkenyl group having 4 to 24 carbon atoms, which may optionally be substituted, provided that the substituents do not significantly adversely affect the lipophilic nature of the group, with the proviso that both $R^1$ and $R^2$ cannot be hydrogen be hydrogen at the same time;

(b) a glycerol-based lipid of general Formula IIIa or IIIb

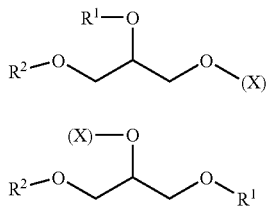

in which $R^1$ and $R^2$ are as defined in general Formula IIa, and

X is a linker group as defined in general Formula I; or (c) a trishydroxymethylmethylamine-based lipid of general Formula IVa or IVb:

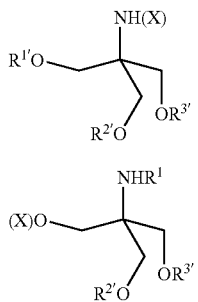

in which $R^1$, $R^2$, and $R^3$ are independently hydrogen or a linear or branched chain alkyl or alkenyl group having 4 to 24 carbon atoms, or an aryl or arylalkyl group having 6 to 24 carbon atoms, said alkyl, alkenyl, aryl or arylalkyl groups may be optionally be substituted, provided that the substitutions do not significantly adversely affect the lipophilic nature of the group, and X is as defined in general Formula I;

with the proviso that at least one of $R^1$, $R^2$, and $R^3$ must not be hydrogen.

9. The compound of claim 7, in which the lipidic moiety L contains one or more charged functional groups.

10. The compound of claim 9, in which the one or more charged functional groups are selected from the group consisting of amidinium, guanidinium, carboxylate, tetrazoline, hydroxamate, hydrazido, ammonium, sulfate, phosphonate, phosphate, and sulfonate.

11. The compound of claim 1, in which S is selected from the group consisting of a mono-, di- or tri-saccharide, and the lipidic moiety is one to three lipoaminoacids of general Formula IIa or IIb:

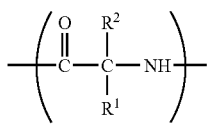

-continued

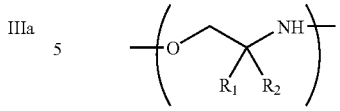

in which each of $R^1$ and $R^2$ may independently be:
(i) hydrogen, or
(ii) a linear or branched chain alkyl or alkenyl group having 4 to 24 carbon atoms, which may optionally be substituted, provided that the substituents do not significantly adversely affect the lipophilic nature of the group,
with the proviso that both $R^1$ and R2 cannot be hydrogen at the same time.

12. The compound of claim 1, in which r is greater than p.

13. The compound of claim 1, in which D is a sulfated oligosaccharide, charged oligosaccharide, sulfated antithrombotic or an aminoglycoside.

14. The compound of claim 12, in which D is a sulfated oligosaccharide, charged oligosaccharide, sulfated antithrombotic or an aminoglycoside.

15. A method of preparing a compound according to claim 1, comprising the step of forming a covalent bond between the mono- or oligosaccharide S and the linker X or the lipid L, in which the bond between S and X is an O-glycoside, C-glycoside, N-glycoside, S-glycoside, amide, urea, thiourea, carbamate, thiocarbamate, carbonate, ether or ester bond, and the bond between X and L is an amide, ester, ether, imine, carbamate, urea, thiourea, or carbonate bond.

16. A composition comprising the compound of claim 1.

17. A method of preparation of a compound according to claim 1, comprising the step of mixing a drug molecule D with $[(W_q—S—X-L)^{(my)}]$ in which W, q, S, X, L, m and y are as defined in claim 1 in solution, followed by removal of the solvent(s) to provide a homogenous mixed salt.

18. The compound of claim 1, in which the compound is piperacillin/2-acetamido-2-deoxy-N-(1-amino-(R/S)dodecoyl)-β-D-glucopyranosyl-amine ionic complex.

19. The compound of claim 1, in which S is a low molecular weight heparin.

20. The compound of claim 19, in which the low molecular weight heparin is selected from the group consisting of fondaparinux, enoxaparin, delteparin, nadroparin and danaparoid.

21. The compound of claim 20, in which the low molecular weight heparin is fondaparinux.

22. The composition of-claim 16, formulated for administration to a human or a domestic or companion animal.

23. The compound of claim 2, wherein D is piperacillin.

24. The compound of claim 1, wherein D is a drug, peptide, mono- or oligosaccharide, or sugar-peptide conjugate.

25. The compound of claim 24, wherein said drug is an antibiotic.

26. The compound of claim 24, wherein said antibiotic is selected from the group consisting of gentamycin sulfate, neomycin, amakacin, tobramycin, netilmicin, and piperacillin.

27. The compound of claim 24, wherein said oligosaccharide is a heparanoid or sulfated oligosaccharide.

28. The compound of claim 27, wherein said oligosaccharide is a low molecular weight heparin.

29. A compound of general Formula I, which is an ionic complex:

  Formula I in which D is a therapeutically useful molecule selected from the group consisting of a sulfated oligosaccharide, a charged oligosaccharide, a sulfated antithrombotic, and an aminoglycoside;

r is an integer greater than or equal to 1;

p, n and m may be the same or different, and are independently integers greater than or equal to 1;

n and m represent the overall magnitude of the charge on the molecules; and z and y are charges, either positive (+) or negative (−), such that when z is positive, y is negative and vice versa;

and $[(W_q\text{—}S\text{—}X\text{-}L)^{(my)}]$ is a carrier compound, in which

X is a covalent bond, or is a linker group, selected from 2 to 14 atom spacers, which may be optionally substituted, branched or linear;

S is a mono- or oligosaccharide;

L is a lipidic moiety;

W is a 3 to 10 atom alkyl or heteroalkyl spacer, which may be branched or linear, and is substituted with one or more functional groups, each of which is charged or is capable of carrying a charge under physiological conditions; and q is an integer, which ranges from 3 to the number of hydroxyls available for substitution on the mono- or oligosaccharide.

30. A lipoamino acid or lipoamino saccharide conjugate of general Formula I:

  Formula I wherein said conjugate forms an ionic complex with a therapeutically-useful drug, D;

r is an integer greater than or equal to 1;

p, n and m may be the same or different, and are independently integers greater than or equal to 1;

n and m represent the overall magnitude of the charge on the molecules; and z and y are charges, either positive (+) or negative (−), such that when z is positive, y is negative and vice versa;

and $[(W_q\text{—}S\text{—}X\text{-}L)^{(my)}]$ is a carrier compound, in which

X is a covalent bond, or is a linker group, selected from 2 to 14 atom spacers, which may be optionally substituted, branched or linear;

S is a mono- or oligosaccharide;

L is a lipidic moiety;

W is a 3 to 10 atom alkyl or heteroalkyl spacer, which may be branched or linear, and is substituted with one or more functional groups, each of which is charged or is capable of carrying a charge under physiological conditions; and q is an integer, which ranges from 3 to the number of hydroxyls available for substitution on the mono- or oligosaccharide.

31. A compound of general Formula I:

  Formula I wherein r is an integer greater than or equal to 1;

n and m may be the same or different, and are independently integers greater than or equal to 1;

n and m represent the overall magnitude of the charge on the molecules; and z and y are charges, either positive (+) or negative (−), such that when z is positive, y is negative and vice versa;

and $[(W_q\text{—}S\text{—}X\text{-}L)^{(my)}]$ is a carrier compound, in which

X is a covalent bond, or is a linker group, selected from 2 to 14 atom spacers, which may be optionally substituted, branched or linear;

S is a mono- or oligosaccharide;

L is a lipidic moiety;

W is a 3 to 10 atom alkyl or heteroalkyl spacer, which may be branched or linear, and is substituted with one or more functional groups, each of which is charged or is capable of carrying a charge under physiological conditions;

q is an integer, which ranges from 3 to the number of hydroxyls available for substitution on the mono- or oligosaccharide; and wherein D is a drug molecule that forms an ionic complex with said compound.

32. The composition of claim 16, further comprising a pharmaceutically-acceptable carrier.

* * * * *